United States Patent
Bennett et al.

(10) Patent No.: US 6,734,017 B2
(45) Date of Patent: May 11, 2004

(54) ANTISENSE MODULATION OF VASCULAR ENDOTHELIAL GROWTH FACTOR RECEPTOR-2 EXPRESSION

(75) Inventors: C. Frank Bennett, Carlsbad, CA (US); Andrew T. Watt, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/967,655

(22) Filed: Sep. 28, 2001

(65) Prior Publication Data

US 2003/0092649 A1 May 15, 2003

(51) Int. Cl.$^7$ .................. C07H 21/02; C07H 21/04; C12N 15/85; C12N 15/86; C12Q 1/68

(52) U.S. Cl. .................. 435/375; 435/6; 435/91.1; 435/325; 536/24.5; 536/24.3; 536/24.31

(58) Field of Search .................. 435/6, 91.1, 91.3, 435/325, 375; 536/23.1, 23.2, 29.3, 29.31, 24.33, 24.5; 514/44

(56) References Cited

U.S. PATENT DOCUMENTS

| | | | |
|---|---|---|---|
| 5,747,651 A | | 5/1998 | Lemischka |
| 5,801,154 A | * | 9/1998 | Baracchini et al. ........... 514/44 |
| 5,830,880 A | | 11/1998 | Sedlacek et al. |
| 5,851,999 A | | 12/1998 | Ullrich et al. |
| 5,861,484 A | | 1/1999 | Kendall et al. |
| 5,994,076 A | * | 11/1999 | Chenchik et al. |
| 6,177,401 B1 | | 1/2001 | Ullrich et al. |
| 6,204,011 B1 | * | 3/2001 | Kendall et al. |
| 6,346,398 B1 | * | 2/2002 | Pavco et al. ............. 435/91.31 |

FOREIGN PATENT DOCUMENTS

| | | | |
|---|---|---|---|
| JP | 2001-46066 | * | 2/2001 |
| WO | WO 94/11499 | | 5/1994 |
| WO | WO 00/75319 | | 12/2000 |
| WO | WO 01/00854 | * | 1/2001 |
| WO | WO 01/44460 | | 6/2001 |
| WO | WO 01/52904 | * | 7/2001 |

OTHER PUBLICATIONS

DW Green et al., American College of Surgeons, "Antisense Oligonucleotides:An Evolving Technology for the Modulation of Gene Expression in Human Disease," Jul. 2000, vol. 191, No. 1, pp. 93–105.*

N Milner et al., Nature Biotechnology, "Selecting effective antisense reagents on combinatorial oligonucleotide arrays," Jun. 1997, vol. 15, pp. 537–541.*

AD Branch, TIBS, "A good antisense molecule is hard to find," Feb. 1998, pp. 45–50.*

S Agrawal et al., Molecular Medicine Today, "Antisense therapeutics:It is as simple as complementary base recognition?" Feb. 2000, vol. 6, pp. 72–81.*

K–Y Jen et al., Stem Cells, "Suppression of Gene Expression by Targeted Disruption of Messenger RNA: Available Options and Current Strategies," 2000, 18:307–319.

PA Pavco et al., Clinical Cancer Research,"Antitumor and Antimetastatic Activity of Ribozymes Targeting the Messenger RNA of Vascular Endothelial Growth Factor Receptors," May 2000, vol. 6, pp. 2094–2103.

TJ Parry et al., Nucleic Acids Research, "Bioactivity of anti–angiogenic ribozymes targeting Flt–1 and KDR mRNA," 1999, vol. 27, No. 13, pp. 2569–2577.

BI Terman et al., Locus Accession L04947, 1991.

Milner et al., "Selecting effective antisense reagents on combinatorial oligonucleotide arrays", nature Biotechnology 1997 15:537–541.

Parry et al., "Bioactivity of anti–angiogenic ribozymes targeting Flt–1 and KDR mRNA", Nucleic Acids Research 1999 27(13):2569–2577.

Payco et al., "Antitumor and Antimetastatic Activity of Ribozymes Targeting the Messenger RNA of Vascular Endothelial Growth Factor Receptors", Clinical Cancer Research 2000 6:2094–2103.

Aiello et al., *Suppression of retinal neovascularization in vivo by inhibition of vascular endothelial growth factor (VEGF) using soluble VEGF–receptor chimeric proteins*, Proc. Natl. Acad. Sci. U. S. A., 1995, 92:10457–10461.

Basu et al., *The neurotransmitter dopamine inhibits angiogenesis induced by vascular permeability factor/vascular endothelial growth factor*, Nat. Med., 2001, 7:569–574.

Berard et al., *Vascular endothelial growth factor confers a growth advantage in vitro and in vivo to stromal cells cultured from neonatal hemangiomas*, Am. J. Pathol., 1997, 150:1315–1326.

Bernatchez et al., *Vascular endothelial growth factor effect on endothelial cell proliferation, migration, and platelet–activating factor synthesis is Flk–1–dependent*, J. Biol. Chem., 1999, 274:31047–31054.

Epstein et al., *Therapeutic interventions for enhancing collateral development by administration of growth factors: basic principles, early results and potential hazards*, Cardiovasc. Res., 2001, 49:532–542.

Graeven et al., *Melanoma–associated expression of vascular endothelial growth factor and its receptors FLT–1 and KDR*, J. Cancer Res. Clin. Oncol., 1999, 125:621–629.

(List continued on next page.)

Primary Examiner—Karen A. Lacourciere
(74) Attorney, Agent, or Firm—Licata & Tyrrell P.C.

(57) ABSTRACT

Antisense compounds, compositions and methods are provided for modulating the expression of vascular endothelial growth factor receptor-2. The compositions comprise antisense compounds, particularly antisense oligonucleotides, targeted to nucleic acids encoding vascular endothelial growth factor receptor-2. Methods of using these compounds for modulation of vascular endothelial growth factor receptor-2 expression and for treatment of diseases associated with expression of vascular endothelial growth factor receptor-2 are provided.

12 Claims, No Drawings

OTHER PUBLICATIONS

Henderson et al., *The basic helix–loop–helix transcription factor HESR1 regulates endothelial cell tube formation*, J. Biol. Chem., 2001, 276:6169–6176.

Kendall et al., *Identification of a natural soluble form of the vascular endothelial growth factor receptor, FLT-1, and its heterodimerization with KDR*, Biochem. Biophys. Res. Commun., 1996, 226:324–328.

Masood et al., *Vascular endothelial growth factor/vascular permeability factor is an autocrine growth factor for AIDS–Kaposi sarcoma*, Proc. Natl. Acad. Sci. U. S. A., 1997, 94:979–984.

Matsuzaki et al., *Vascular endothelial growth factor rescues hippocampal neurons from glutamate–induced toxicity: signal transduction cascades*, Faseb J., 2001, 12:12.

Matthews et al., *A receptor tyrosine kinase cDNA isolated from a population of enriched primitive hematopoietic cells and exhibiting close genetic linkage to c–kit*, Proc. Natl. Acad. Sci. U. S. A., 1991, 88:9026–9030.

Millauer et al., *Glioblastoma growth inhibited in vivo by a dominant–negative Flk–1 mutant*, Nature, 1994, 367:576–579.

Millauer et al., *High affinity VEGF binding and developmental expression suggest Flk–1 as a major regulator of vasculogenesis and angiogenesis*, Cell, 1993, 72:835–846.

Robert et al., *Coexpression of neuropilin–1, Flk1, and VEGF (164) in developing and mature mouse kidney glomeruli*, Am. J. Physiol. Renal Physiol., 2000, 279:F275–282.

Roeckl et al., *Differential binding characteristics and cellular inhibition by soluble VEGF receptors 1 and 2*, Exp. Cell Res., 1998, 241:161–170.

Schuh et al., *In vivo hematopoietic and endothelial potential of flk–1 (–/–) embryonic stem cells and embryos*, Proc. Natl. Acad. Sci. U. S. A., 1999, 96:2159–2164.

Shalaby et al., *Failure of blood–island formation and vasculogenesis in Flk–1–deficient mice*, Nature, 1995, 376:62–66.

Shibuya, *Structure and dual function of vascular endothelial growth factor receptor–1 (Flt–1)*, Int. J. Biochem. Cell Biol., 2001, 33:409–420.

Skobe et al., *Halting angiogenesis suppresses carcinoma cell invasion*, Nat. Med., 1997, 3:1222–1227.

Spritz et al., *A YAC contig spanning a cluster of human type III receptor protein tyrosine kinase genes (PDGFRA–KIT–KDR) in chromosome segment 4q12*, Genomics, 1994, 22:431–436.

Terman et al., *Identification of a new endothelial cell growth factor receptor tyrosine kinase*, Oncogene, 1991, 6:1677–1683.

Wada et al., *Expression of vascular endothelial growth factor and its receptor (KDR/flk–1) mRNA in experimental choroidal neovascularization*, Curr. Eye Res., 1999, 18:203–213.

Wu et al., *Utilization of distinct signaling pathways by receptors for vascular endothelial cell growth factor and other mitogens in the induction of endothelial cell proliferation*, J. Biol. Chem., 2000, 275:5096–5103.

Zachary et al., *Signaling transduction mechanisms mediating biological actions of the vascular endothelial growth factor family*, Cardiovasc. Res., 2001, 49:568–581.

Ziegler et al., *KDR receptor: a key marker defining hematopoietic stem cells*, Science, 1999, 285:1553–1558.

\* cited by examiner

SEQUENCE LISTING

<160> NUMBER OF SEQ ID NOS: 95

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                           20

```
<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                 20

<210> SEQ ID NO 3
<211> LENGTH: 5830
<212> TYPE: DNA
<213> ORGANISM: Homo sapiens
<220> FEATURE:
<221> NAME/KEY: CDS
<222> LOCATION: (304)...(4374)

<400> SEQUENCE: 3
actgagtccc gggaccccgg gagagcggtc agtgtgtggt cgctgcgttt cctctgcctg    60
cgccgggcat cacttgcgcg ccgcagaaag tccgtctggc agcctggata tcctctccta   120
ccggcacccg cagacgcccc tgcagccgcc ggtcggcgcc cgggctccct agccctgtgc   180
gctcaactgt cctgcgctgc ggggtgccgc gagttccacc tccgcgcctc cttctctaga   240
caggcgctgg gagaaagaac cggctcccga gttctgggca tttcgcccgg ctcgaggtgc   300 agg atg cag agc aag gtg ctg ctg gcc gtc gcc ctg tgg ctc tgc gtg    348
    Met Gln Ser Lys Val Leu Leu Ala Val Ala Leu Trp Leu Cys Val
      1               5                  10                  15 gag acc cgg gcc gcc tct gtg ggt ttg cct agt gtt tct ctt gat ctg    396
Glu Thr Arg Ala Ala Ser Val Gly Leu Pro Ser Val Ser Leu Asp Leu
                 20                  25                  30 ccc agg ctc agc ata caa aaa gac ata ctt aca att aag gct aat aca    444
Pro Arg Leu Ser Ile Gln Lys Asp Ile Leu Thr Ile Lys Ala Asn Thr
             35                  40                  45 act ctt caa att act tgc agg gga cag agg gac ttg gac tgg ctt tgg    492
Thr Leu Gln Ile Thr Cys Arg Gly Gln Arg Asp Leu Asp Trp Leu Trp
         50                  55                  60 ccc aat aat cag agt ggc agt gag caa agg gtg gag gtg act gag tgc    540
Pro Asn Asn Gln Ser Gly Ser Glu Gln Arg Val Glu Val Thr Glu Cys
     65                  70                  75 agc gat ggc ctc ttc tgt aag aca ctc aca att cca aaa gtg atc gga    588
Ser Asp Gly Leu Phe Cys Lys Thr Leu Thr Ile Pro Lys Val Ile Gly
 80                  85                  90                  95 aat gac act gga gcc tac aag tgc ttc tac cgg gaa act gac ttg gcc    636
Asn Asp Thr Gly Ala Tyr Lys Cys Phe Tyr Arg Glu Thr Asp Leu Ala
                100                 105                 110 tcg gtc att tat gtc tat gtt caa gat tac aga tct cca ttt att gct    684
Ser Val Ile Tyr Val Tyr Val Gln Asp Tyr Arg Ser Pro Phe Ile Ala
            115                 120                 125 tct gtt agt gac caa cat gga gtc gtg tac att act gag aac aaa aac    732
Ser Val Ser Asp Gln His Gly Val Val Tyr Ile Thr Glu Asn Lys Asn
        130                 135                 140 aaa act gtg gtg att cca tgt ctc ggg tcc att tca aat ctc aac gtg    780
Lys Thr Val Val Ile Pro Cys Leu Gly Ser Ile Ser Asn Leu Asn Val
    145                 150                 155 tca ctt tgt gca aga tac cca gaa aag aga ttt gtt cct gat ggt aac    828
Ser Leu Cys Ala Arg Tyr Pro Glu Lys Arg Phe Val Pro Asp Gly Asn
160                 165                 170                 175 aga att tcc tgg gac agc aag aag ggc ttt act att ccc agc tac atg    876
Arg Ile Ser Trp Asp Ser Lys Lys Gly Phe Thr Ile Pro Ser Tyr Met
                180                 185                 190
```

```
atc agc tat gct ggc atg gtc ttc tgt gaa gca aaa att aat gat gaa      924
Ile Ser Tyr Ala Gly Met Val Phe Cys Glu Ala Lys Ile Asn Asp Glu
            195                 200                 205 agt tac cag tct att atg tac ata gtt gtc gtt gta ggg tat agg att      972
Ser Tyr Gln Ser Ile Met Tyr Ile Val Val Val Val Gly Tyr Arg Ile
        210                 215                 220 tat gat gtg gtt ctg agt ccg tct cat gga att gaa cta tct gtt gga     1020
Tyr Asp Val Val Leu Ser Pro Ser His Gly Ile Glu Leu Ser Val Gly
225                 230                 235 gaa aag ctt gtc tta aat tgt aca gca aga act gaa cta aat gtg ggg     1068
Glu Lys Leu Val Leu Asn Cys Thr Ala Arg Thr Glu Leu Asn Val Gly
240                 245                 250                 255 att gac ttc aac tgg gaa tac cct tct tcg aag cat cag cat aag aaa     1116
Ile Asp Phe Asn Trp Glu Tyr Pro Ser Ser Lys His Gln His Lys Lys
                260                 265                 270 ctt gta aac cga gac cta aaa acc cag tct ggg agt gag atg aag aaa     1164
Leu Val Asn Arg Asp Leu Lys Thr Gln Ser Gly Ser Glu Met Lys Lys
            275                 280                 285 ttt ttg agc acc tta act ata gat ggt gta acc cgg agt gac caa gga     1212
Phe Leu Ser Thr Leu Thr Ile Asp Gly Val Thr Arg Ser Asp Gln Gly
        290                 295                 300 ttg tac acc tgt gca gca tcc agt ggg ctg atg acc aag aag aac agc     1260
Leu Tyr Thr Cys Ala Ala Ser Ser Gly Leu Met Thr Lys Lys Asn Ser
305                 310                 315 aca ttt gtc agg gtc cat gaa aaa cct ttt gtt gct ttt gga agt ggc     1308
Thr Phe Val Arg Val His Glu Lys Pro Phe Val Ala Phe Gly Ser Gly
320                 325                 330                 335 atg gaa tct ctg gtg gaa gcc acg gtg ggg gag cgt gtc aga atc cct     1356
Met Glu Ser Leu Val Glu Ala Thr Val Gly Glu Arg Val Arg Ile Pro
                340                 345                 350 gcg aag tac ctt ggt tac cca ccc cca gaa ata aaa tgg tat aaa aat     1404
Ala Lys Tyr Leu Gly Tyr Pro Pro Pro Glu Ile Lys Trp Tyr Lys Asn
            355                 360                 365 gga ata ccc ctt gag tcc aat cac aca att aaa gcg ggg cat gta ctg     1452
Gly Ile Pro Leu Glu Ser Asn His Thr Ile Lys Ala Gly His Val Leu
        370                 375                 380 acg att atg gaa gtg agt gaa aga gac aca gga aat tac act gtc atc     1500
Thr Ile Met Glu Val Ser Glu Arg Asp Thr Gly Asn Tyr Thr Val Ile
385                 390                 395 ctt acc aat ccc att tca aag gag aag cag agc cat gtg gtc tct ctg     1548
Leu Thr Asn Pro Ile Ser Lys Glu Lys Gln Ser His Val Val Ser Leu
400                 405                 410                 415 gtt gtg tat gtc cca ccc cag att ggt gag aaa tct cta atc tct cct     1596
Val Val Tyr Val Pro Pro Gln Ile Gly Glu Lys Ser Leu Ile Ser Pro
                420                 425                 430 gtg gat tcc tac cag tac ggc acc act caa acg ctg aca tgt acg gtc     1644
Val Asp Ser Tyr Gln Tyr Gly Thr Thr Gln Thr Leu Thr Cys Thr Val
            435                 440                 445 tat gcc att cct ccc ccg cat cac atc cac tgg tat tgg cag ttg gag     1692
Tyr Ala Ile Pro Pro Pro His His Ile His Trp Tyr Trp Gln Leu Glu
        450                 455                 460 gaa gag tgc gcc aac gag ccc agc caa gct gtc tca gtg aca aac cca     1740
Glu Glu Cys Ala Asn Glu Pro Ser Gln Ala Val Ser Val Thr Asn Pro
465                 470                 475 tac cct tgt gaa gaa tgg aga agt gtg gag gac ttc cag gga gga aat     1788
Tyr Pro Cys Glu Glu Trp Arg Ser Val Glu Asp Phe Gln Gly Gly Asn
480                 485                 490                 495 aaa att gaa gtt aat aaa aat caa ttt gct cta att gaa gga aaa aac     1836
Lys Ile Glu Val Asn Lys Asn Gln Phe Ala Leu Ile Glu Gly Lys Asn
                500                 505                 510
```

| | |
|---|---|
| aaa act gta agt acc ctt gtt atc caa gcg gca aat gtg tca gct ttg<br>Lys Thr Val Ser Thr Leu Val Ile Gln Ala Ala Asn Val Ser Ala Leu<br>515                    520                    525 | 1884 |
| tac aaa tgt gaa gcg gtc aac aaa gtc ggg aga gga gag agg gtg atc<br>Tyr Lys Cys Glu Ala Val Asn Lys Val Gly Arg Gly Glu Arg Val Ile<br>530                    535                    540 | 1932 |
| tcc ttc cac gtg acc agg ggt cct gaa att act ttg caa cct gac atg<br>Ser Phe His Val Thr Arg Gly Pro Glu Ile Thr Leu Gln Pro Asp Met<br>545                    550                    555 | 1980 |
| cag ccc act gag cag gag agc gtg tct ttg tgg tgc act gca gac aga<br>Gln Pro Thr Glu Gln Glu Ser Val Ser Leu Trp Cys Thr Ala Asp Arg<br>560                    565                    570                    575 | 2028 |
| tct acg ttt gag aac ctc aca tgg tac aag ctt ggc cca cag cct ctg<br>Ser Thr Phe Glu Asn Leu Thr Trp Tyr Lys Leu Gly Pro Gln Pro Leu<br>580                    585                    590 | 2076 |
| cca atc cat gtg gga gag ttg ccc aca cct gtt tgc aag aac ttg gat<br>Pro Ile His Val Gly Glu Leu Pro Thr Pro Val Cys Lys Asn Leu Asp<br>595                    600                    605 | 2124 |
| act ctt tgg aaa ttg aat gcc acc atg ttc tct aat agc aca aat gac<br>Thr Leu Trp Lys Leu Asn Ala Thr Met Phe Ser Asn Ser Thr Asn Asp<br>610                    615                    620 | 2172 |
| att ttg atc atg gag ctt aag aat gca tcc ttg cag gac caa gga gac<br>Ile Leu Ile Met Glu Leu Lys Asn Ala Ser Leu Gln Asp Gln Gly Asp<br>625                    630                    635 | 2220 |
| tat gtc tgc ctt gct caa gac agg aag acc aag aaa aga cat tgc gtg<br>Tyr Val Cys Leu Ala Gln Asp Arg Lys Thr Lys Lys Arg His Cys Val<br>640                    645                    650                    655 | 2268 |
| gtc agg cag ctc aca gtc cta gag cgt gtg gca ccc acg atc aca gga<br>Val Arg Gln Leu Thr Val Leu Glu Arg Val Ala Pro Thr Ile Thr Gly<br>660                    665                    670 | 2316 |
| aac ctg gag aat cag acg aca agt att ggg gaa agc atc gaa gtc tca<br>Asn Leu Glu Asn Gln Thr Thr Ser Ile Gly Glu Ser Ile Glu Val Ser<br>675                    680                    685 | 2364 |
| tgc acg gca tct ggg aat ccc cct cca cag atc atg tgg ttt aaa gat<br>Cys Thr Ala Ser Gly Asn Pro Pro Pro Gln Ile Met Trp Phe Lys Asp<br>690                    695                    700 | 2412 |
| aat gag acc ctt gta gaa gac tca ggc att gta ttg aag gat ggg aac<br>Asn Glu Thr Leu Val Glu Asp Ser Gly Ile Val Leu Lys Asp Gly Asn<br>705                    710                    715 | 2460 |
| cgg aac ctc act atc cgc aga gtg agg aag gag gac gaa ggc ctc tac<br>Arg Asn Leu Thr Ile Arg Arg Val Arg Lys Glu Asp Glu Gly Leu Tyr<br>720                    725                    730                    735 | 2508 |
| acc tgc cag gca tgc agt gtt ctt ggc tgt gca aaa gtg gag gca ttt<br>Thr Cys Gln Ala Cys Ser Val Leu Gly Cys Ala Lys Val Glu Ala Phe<br>740                    745                    750 | 2556 |
| ttc ata ata gaa ggt gcc cag gaa aag acg aac ttg gaa atc att att<br>Phe Ile Ile Glu Gly Ala Gln Glu Lys Thr Asn Leu Glu Ile Ile Ile<br>755                    760                    765 | 2604 |
| cta gta ggc acg gcg gtg att gcc atg ttc ttc tgg cta ctt ctt gtc<br>Leu Val Gly Thr Ala Val Ile Ala Met Phe Phe Trp Leu Leu Leu Val<br>770                    775                    780 | 2652 |
| atc atc cta cgg acc gtt aag cgg gcc aat gga ggg gaa ctg aag aca<br>Ile Ile Leu Arg Thr Val Lys Arg Ala Asn Gly Gly Glu Leu Lys Thr<br>785                    790                    795 | 2700 |
| ggc tac ttg tcc atc gtc atg gat cca gat gaa ctc cca ttg gat gaa<br>Gly Tyr Leu Ser Ile Val Met Asp Pro Asp Glu Leu Pro Leu Asp Glu<br>800                    805                    810                    815 | 2748 |
| cat tgt gaa cga ctg cct tat gat gcc agc aaa tgg gaa ttc ccc aga<br>His Cys Glu Arg Leu Pro Tyr Asp Ala Ser Lys Trp Glu Phe Pro Arg | 2796 |

-continued

|     |     | 820 |     |     |     | 825 |     |     |     | 830 |     |      |
|-----|-----|-----|-----|-----|-----|-----|-----|-----|-----|-----|-----|------|
| gac | cgg | ctg | aag | cta | ggt | aag | cct | ctt | ggc | cgt | ggt | gcc | ttt | ggc | caa | 2844 |
| Asp | Arg | Leu | Lys | Leu | Gly | Lys | Pro | Leu | Gly | Arg | Gly | Ala | Phe | Gly | Gln |      |
|     |     | 835 |     |     |     | 840 |     |     |     | 845 |     |      | gac cgg ctg aag cta ggt aag cct ctt ggc cgt ggt gcc ttt ggc caa  2844
Asp Arg Leu Lys Leu Gly Lys Pro Leu Gly Arg Gly Ala Phe Gly Gln
        835             840             845 gtg att gaa gca gat gcc ttt gga att gac aag aca gca act tgc agg  2892
Val Ile Glu Ala Asp Ala Phe Gly Ile Asp Lys Thr Ala Thr Cys Arg
        850             855             860 aca gta gca gtc aaa atg ttg aaa gaa gga gca aca cac agt gag cat  2940
Thr Val Ala Val Lys Met Leu Lys Glu Gly Ala Thr His Ser Glu His
        865             870             875 cga gct ctc atg tct gaa ctc aag atc ctc att cat att ggt cac cat  2988
Arg Ala Leu Met Ser Glu Leu Lys Ile Leu Ile His Ile Gly His His
880             885             890             895 ctc aat gtg gtc aac ctt cta ggt gcc tgt acc aag cca gga ggg cca  3036
Leu Asn Val Val Asn Leu Leu Gly Ala Cys Thr Lys Pro Gly Gly Pro
        900             905             910 ctc atg gtg att gtg gaa ttc tgc aaa ttt gga aac ctg tcc act tac  3084
Leu Met Val Ile Val Glu Phe Cys Lys Phe Gly Asn Leu Ser Thr Tyr
        915             920             925 ctg agg agc aag aga aat gaa ttt gtc ccc tac aag acc aaa ggg gca  3132
Leu Arg Ser Lys Arg Asn Glu Phe Val Pro Tyr Lys Thr Lys Gly Ala
        930             935             940 cga ttc cgt caa ggg aaa gac tac gtt gga gca atc cct gtg gat ctg  3180
Arg Phe Arg Gln Gly Lys Asp Tyr Val Gly Ala Ile Pro Val Asp Leu
945             950             955 aaa cgg cgc ttg gac agc atc acc agt agc cag agc tca gcc agc tct  3228
Lys Arg Arg Leu Asp Ser Ile Thr Ser Ser Gln Ser Ser Ala Ser Ser
960             965             970             975 gga ttt gtg gag gag aag tcc ctc agt gat gta gaa gaa gag gaa gct  3276
Gly Phe Val Glu Glu Lys Ser Leu Ser Asp Val Glu Glu Glu Glu Ala
        980             985             990 cct gaa gat ctg tat aag gac ttc ctg acc ttg gag cat ctc atc tgt  3324
Pro Glu Asp Leu Tyr Lys Asp Phe Leu Thr Leu Glu His Leu Ile Cys
        995             1000            1005 tac agc ttc caa gtg gct aag ggc atg gag ttc ttg gca tcg cga aag  3372
Tyr Ser Phe Gln Val Ala Lys Gly Met Glu Phe Leu Ala Ser Arg Lys
        1010            1015            1020 tgt atc cac agg gac ctg gcg gca cga aat atc ctc tta tcg gag aag  3420
Cys Ile His Arg Asp Leu Ala Ala Arg Asn Ile Leu Leu Ser Glu Lys
        1025            1030            1035 aac gtg gtt aaa atc tgt gac ttt ggc ttg gcc cgg gat att tat aaa  3468
Asn Val Val Lys Ile Cys Asp Phe Gly Leu Ala Arg Asp Ile Tyr Lys
1040            1045            1050            1055 gat cca gat tat gtc aga aaa gga gat gct cgc ctc cct ttg aaa tgg  3516
Asp Pro Asp Tyr Val Arg Lys Gly Asp Ala Arg Leu Pro Leu Lys Trp
        1060            1065            1070 atg gcc cca gaa aca att ttt gac aga gtg tac aca atc cag agt gac  3564
Met Ala Pro Glu Thr Ile Phe Asp Arg Val Tyr Thr Ile Gln Ser Asp
        1075            1080            1085 gtc tgg tct ttt ggt gtt ttg ctg tgg gaa ata ttt tcc tta ggt gct  3612
Val Trp Ser Phe Gly Val Leu Leu Trp Glu Ile Phe Ser Leu Gly Ala
        1090            1095            1100 tct cca tat cct ggg gta aag att gat gaa gaa ttt tgt agg cga ttg  3660
Ser Pro Tyr Pro Gly Val Lys Ile Asp Glu Glu Phe Cys Arg Arg Leu
1105            1110            1115 aaa gaa gga act aga atg agg gcc cct gat tat act aca cca gaa atg  3708
Lys Glu Gly Thr Arg Met Arg Ala Pro Asp Tyr Thr Thr Pro Glu Met
1120            1125            1130            1135 tac cag acc atg ctg gac tgc tgg cac ggg gag ccc agt cag aga ccc  3756

-continued

```
Tyr Gln Thr Met Leu Asp Cys Trp His Gly Glu Pro Ser Gln Arg Pro
            1140                1145                1150 acg ttt tca gag ttg gtg gaa cat ttg gga aat ctc ttg caa gct aat      3804
Thr Phe Ser Glu Leu Val Glu His Leu Gly Asn Leu Leu Gln Ala Asn
        1155                1160                1165 gct cag cag gat ggc aaa gac tac att gtt ctt ccg ata tca gag act      3852
Ala Gln Gln Asp Gly Lys Asp Tyr Ile Val Leu Pro Ile Ser Glu Thr
    1170                1175                1180 ttg agc atg gaa gag gat tct gga ctc tct ctg cct acc tca cct gtt      3900
Leu Ser Met Glu Glu Asp Ser Gly Leu Ser Leu Pro Thr Ser Pro Val
1185                1190                1195 tcc tgt atg gag gag gag gaa gta tgt gac ccc aaa ttc cat tat gac      3948
Ser Cys Met Glu Glu Glu Glu Val Cys Asp Pro Lys Phe His Tyr Asp
1200                1205                1210                1215 aac aca gca gga atc agt cag tat ctg cag aac agt aag cga aag agc      3996
Asn Thr Ala Gly Ile Ser Gln Tyr Leu Gln Asn Ser Lys Arg Lys Ser
                1220                1225                1230 cgg cct gtg agt gta aaa aca ttt gaa gat atc ccg tta gaa gaa cca      4044
Arg Pro Val Ser Val Lys Thr Phe Glu Asp Ile Pro Leu Glu Glu Pro
            1235                1240                1245 gaa gta aaa gta atc cca gat gac aac cag acg gac agt ggt atg gtt      4092
Glu Val Lys Val Ile Pro Asp Asp Asn Gln Thr Asp Ser Gly Met Val
        1250                1255                1260 ctt gcc tca gaa gag ctg aaa act ttg gaa gac aga acc aaa tta tct      4140
Leu Ala Ser Glu Glu Leu Lys Thr Leu Glu Asp Arg Thr Lys Leu Ser
    1265                1270                1275 cca tct ttt ggt gga atg gtg ccc agc aaa agc agg gag tct gtg gca      4188
Pro Ser Phe Gly Gly Met Val Pro Ser Lys Ser Arg Glu Ser Val Ala
1280                1285                1290                1295 tct gaa ggc tca aac cag aca agc ggc tac cag tcc gga tat cac tcc      4236
Ser Glu Gly Ser Asn Gln Thr Ser Gly Tyr Gln Ser Gly Tyr His Ser
                1300                1305                1310 gat gac aca gac acc acc gtg tac tcc agt gag gaa gca gaa ctt tta      4284
Asp Asp Thr Asp Thr Thr Val Tyr Ser Ser Glu Glu Ala Glu Leu Leu
            1315                1320                1325 aag ctg ata gag att gga gtg caa acc ggt agc aca gcc cag att ctc      4332
Lys Leu Ile Glu Ile Gly Val Gln Thr Gly Ser Thr Ala Gln Ile Leu
        1330                1335                1340 cag cct gac tcg ggg acc aca ctg agc tct cct cct gtt taa aaggaagcat   4384
Gln Pro Asp Ser Gly Thr Thr Leu Ser Ser Pro Pro Val
    1345                1350                1355 ccacacccca actcccggac atcacatgag aggtctgctc agattttgaa gtgttgttct    4444
ttccaccagc aggaagtagc cgcatttgat tttcatttcg acaacagaaa aaggacctcg    4504
gactgcaggg agccagtctt ctaggcatat cctggaagag gcttgtgacc caagaatgtg    4564
tctgtgtctt ctcccagtgt tgacctgatc ctctttttc attcatttaa aaagcattat     4624
catgcccctg ctgcgggtct caccatgggt ttagaacaaa gagcttcaag caatggcccc    4684
atcctcaaag aagtagcagt acctgggag ctgacacttc tgtaaaacta gaagataaac     4744
caggcaacgt aagtgttcga ggtgttgaag atgggaagga tttgcagggc tgagtctatc    4804
caagaggctt tgtttaggac gtgggtccca agccaagcct taagtgtgga attcggattg    4864
atagaaagga agactaacgt taccttgctt tggagagtac tggagcctgc aaatgcattg    4924
tgtttgctct ggtggaggtg ggcatgggt ctgttctgaa atgtaaaggg ttcagacggg      4984
gtttctggtt ttagaaggtt gcgtgttctt cgagttgggc taaagtagag ttcgttgtgc    5044
tgtttctgac tcctaatgag agttccttcc agaccgttag ctgtctcctt gccaagcccc    5104
```

-continued

```
aggaagaaaa tgatgcagct ctggctcctt gtctcccagg ctgatccttt attcagaata    5164
ccacaaagaa aggacattca gctcaaggct ccctgccgtg ttgaagagtt ctgactgcac    5224
aaaccagctt ctggtttctt ctggaatgaa taccctcata tctgtcctga tgtgatatgt    5284
ctgagactga atgcgggagg ttcaatgtga agctgtgtgt ggtgtcaaag tttcaggaag    5344
gattttaccc ttttgttctt cccctgtcc caacccact ctcacccgc aacccatcag       5404 tattttagtt atttggcctc tactccagta aacctgattg ggtttgttca ctctctgaat    5464
gattattagc cagacttcaa aattatttta tagcccaaat tataacatct attgtattat    5524
ttagactttt aacatataga gctatttcta ctgattttg ccttgttct gtccttttt      5584 tcaaaaaaga aatgtgttt tttgtttggt accatagtgt gaaatgctgg gaacaatgac    5644
tataagacat gctatggcac atatatttat agtctgttta tgtagaaaca aatgtaatat    5704
attaaagcct tatatataat gaactttgta ctattcacat tttgtatcag tattatgtag    5764
cataacaaag gtcataatgc tttcagcaat tgatgtcatt ttattaaaga acattgaaaa    5824
acttga                                                                5830
```

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
aaccagacaa gcggctacca                                                  20

<210> SEQ ID NO 5
<211> LENGTH: 29
<212> TYPE: DNA
<213> ORGANISM: Artificial Sequence
<220> FEATURE:
<223> OTHER INFORMATION: PCR Primer

<400> SEQUENCE: 5
ctccaatctc tatcagcttt aaaagttct                                        29

<210> SEQ ID NO 6
<211> LENGTH: 25
<212> TYPE: DNA
<213> ORGANISM: Artificial Sequence
<220> FEATURE:
<223> OTHER INFORMATION: PCR Probe

<400> SEQUENCE: 6
cactccgatg acacagacac caccg                                            25

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                   19

<210> SEQ ID NO 8
<211> LENGTH: 20
<212> TYPE: DNA
<213> ORGANISM: Artificial Sequence -continued

```
<220> FEATURE:
<223> OTHER INFORMATION: PCR Primer

<400> SEQUENCE: 8
gaagatggtg atgggatttc                                                    20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                    20

<210> SEQ ID NO 10
<211> LENGTH: 5470
<212> TYPE: DNA
<213> ORGANISM: Mus musculus
<220> FEATURE:
<221> NAME/KEY: CDS
<222> LOCATION: (286)...(4389)

<400> SEQUENCE: 10
tatagggcga attgggtacg ggaccccct cgaggtcgac ggtatcgata agcttgatat        60
cgaattcggg cccagactgt gtcccgcagc cgggataacc tggctgaccc gattccgcgg      120
acaccgctga cagccgcggc tggagccagg cgccggtgc cccgcgctct ccccggtctt        180
gcgctgcggg ggccataccg cctctgtgac ttctttgcgg gccagggacg agaaggagt        240 ctgtgcctga gaaactgggc tctgtgccca ggcgcgaggt gcagg atg gag agc aag      297
                                                   Met Glu Ser Lys
                                                     1 gcg ctg cta gct gtc gct ctg tgg ttc tgc gtg gag acc cga gcc gcc         345
Ala Leu Leu Ala Val Ala Leu Trp Phe Cys Val Glu Thr Arg Ala Ala
  5                  10                  15                  20 tct gtg ggt ttg act ggc gat ttt ctc cat ccc ccc aag ctc agc aca         393
Ser Val Gly Leu Thr Gly Asp Phe Leu His Pro Pro Lys Leu Ser Thr
             25                  30                  35 cag aaa gac ata ctg aca att ttg gca aat aca acc ctt cag att act         441
Gln Lys Asp Ile Leu Thr Ile Leu Ala Asn Thr Thr Leu Gln Ile Thr
         40                  45                  50 tgc agg gga cag cgg gac ctg gac tgg ctt tgg ccc aat gct cag cgt         489
Cys Arg Gly Gln Arg Asp Leu Asp Trp Leu Trp Pro Asn Ala Gln Arg
     55                  60                  65 gat tct gag gaa agg gta ttg gtg act gaa tgc ggc ggt ggt gac agt         537
Asp Ser Glu Glu Arg Val Leu Val Thr Glu Cys Gly Gly Gly Asp Ser
 70                  75                  80 atc ttc tgc aaa aca ctc acc att ccc agg gtg gtt gga aat gat act         585
Ile Phe Cys Lys Thr Leu Thr Ile Pro Arg Val Val Gly Asn Asp Thr
 85                  90                  95                 100 gga gcc tac aag tgc tcg tac cgg gac gtc gac ata gcc tcc act gtt         633
Gly Ala Tyr Lys Cys Ser Tyr Arg Asp Val Asp Ile Ala Ser Thr Val
                105                 110                 115 tat gtc tat gtt cga gat tac aga tca cca ttc atc gcc tct gtc agt         681
Tyr Val Tyr Val Arg Asp Tyr Arg Ser Pro Phe Ile Ala Ser Val Ser
            120                 125                 130 gac cag cat ggc atc gtg tac atc acc gag aac aag aac aaa act gtg         729
Asp Gln His Gly Ile Val Tyr Ile Thr Glu Asn Lys Asn Lys Thr Val
        135                 140                 145 gtg atc ccc tgc cga ggg tcg att tca aac ctc aat gtg tct ctt tgc         777
```

```
Val Ile Pro Cys Arg Gly Ser Ile Ser Asn Leu Asn Val Ser Leu Cys
    150                 155                 160 gct agg tat cca gaa aag aga ttt gtt ccg gat gga aac aga att tcc      825
Ala Arg Tyr Pro Glu Lys Arg Phe Val Pro Asp Gly Asn Arg Ile Ser
165                 170                 175                 180 tgg gac agc gag ata ggc ttt act ctc ccc agt tac atg atc agc tat      873
Trp Asp Ser Glu Ile Gly Phe Thr Leu Pro Ser Tyr Met Ile Ser Tyr
                    185                 190                 195 gcc ggc atg gtc ttc tgt gag gca aag atc aat gat gaa acc tat cag      921
Ala Gly Met Val Phe Cys Glu Ala Lys Ile Asn Asp Glu Thr Tyr Gln
                200                 205                 210 tct atc atg tac ata gtt gtg gtt gta gga tat agg att tat gat gtg      969
Ser Ile Met Tyr Ile Val Val Val Val Gly Tyr Arg Ile Tyr Asp Val
            215                 220                 225 att ctg agc ccc ccg cat gaa att gag cta tct gcc gga gaa aaa ctt     1017
Ile Leu Ser Pro Pro His Glu Ile Glu Leu Ser Ala Gly Glu Lys Leu
        230                 235                 240 gtc tta aat tgt aca gcg aga aca gag ctc aat gtg ggg ctt gat ttc     1065
Val Leu Asn Cys Thr Ala Arg Thr Glu Leu Asn Val Gly Leu Asp Phe
245                 250                 255                 260 acc tgg cac tct cca cct tca aag tct cat cat aag aag att gta aac     1113
Thr Trp His Ser Pro Pro Ser Lys Ser His His Lys Lys Ile Val Asn
                    265                 270                 275 cgg gat gtg aaa ccc ttt cct ggg act gtg gcg aag atg ttt ttg agc     1161
Arg Asp Val Lys Pro Phe Pro Gly Thr Val Ala Lys Met Phe Leu Ser
                280                 285                 290 acc ttg aca ata gaa agt gtg acc aag agt gac caa ggg gaa tac acc     1209
Thr Leu Thr Ile Glu Ser Val Thr Lys Ser Asp Gln Gly Glu Tyr Thr
            295                 300                 305 tgt gta gcg tcc agt gga cgg atg atc aag aga aat aga aca ttt gtc     1257
Cys Val Ala Ser Ser Gly Arg Met Ile Lys Arg Asn Arg Thr Phe Val
        310                 315                 320 cga gtt cac aca aag cct ttt att gct ttc ggt agt ggg atg aaa tct     1305
Arg Val His Thr Lys Pro Phe Ile Ala Phe Gly Ser Gly Met Lys Ser
325                 330                 335                 340 ttg gtg gaa gcc aca gtg ggc agt caa gtc cga atc cct gtg aag tat     1353
Leu Val Glu Ala Thr Val Gly Ser Gln Val Arg Ile Pro Val Lys Tyr
                    345                 350                 355 ctc agt tac cca gct cct gat atc aaa tgg tac aga aat gga agg ccc     1401
Leu Ser Tyr Pro Ala Pro Asp Ile Lys Trp Tyr Arg Asn Gly Arg Pro
                360                 365                 370 att gag tcc aac tac aca atg att gtt ggc gat gaa ctc acc atc atg     1449
Ile Glu Ser Asn Tyr Thr Met Ile Val Gly Asp Glu Leu Thr Ile Met
            375                 380                 385 gaa gtg act gaa aga gat gca gga aac tac acg gtc atc ctc acc aac     1497
Glu Val Thr Glu Arg Asp Ala Gly Asn Tyr Thr Val Ile Leu Thr Asn
390                 395                 400 ccc att tca atg gag aaa cag agc cac atg gtc tct ctg gtt gtg aat     1545
Pro Ile Ser Met Glu Lys Gln Ser His Met Val Ser Leu Val Val Asn
405                 410                 415                 420 gtc cca ccc cag atc ggt gag aaa gcc ttg atc tcg cct atg gat tcc     1593
Val Pro Pro Gln Ile Gly Glu Lys Ala Leu Ile Ser Pro Met Asp Ser
                    425                 430                 435 tac cag tat ggg acc atg cag aca ttg aca tgc aca gtc tac gcc aac     1641
Tyr Gln Tyr Gly Thr Met Gln Thr Leu Thr Cys Thr Val Tyr Ala Asn
                440                 445                 450 cct ccc ctg cac cac atc cag tgg tac tgg cag cta gaa gaa gcc tgc     1689
Pro Pro Leu His His Ile Gln Trp Tyr Trp Gln Leu Glu Glu Ala Cys
            455                 460                 465
```

```
tcc tac aga ccc ggc caa aca agc ccg tat gct tgt aaa gaa tgg aga    1737
Ser Tyr Arg Pro Gly Gln Thr Ser Pro Tyr Ala Cys Lys Glu Trp Arg
    470                 475                 480 cac gtg gag gat ttc cag ggg gga aac aag atc gaa gtc acc aaa aac    1785
His Val Glu Asp Phe Gln Gly Gly Asn Lys Ile Glu Val Thr Lys Asn
485                 490                 495                 500 caa tat gcc ctg att gaa gga aaa aac aaa act gta agt acg ctg gtc    1833
Gln Tyr Ala Leu Ile Glu Gly Lys Asn Lys Thr Val Ser Thr Leu Val
                505                 510                 515 atc caa gct gcc aac gtg tca gcg ttg tac aaa tgt gaa gcc atc aac    1881
Ile Gln Ala Ala Asn Val Ser Ala Leu Tyr Lys Cys Glu Ala Ile Asn
        520                 525                 530 aaa gcg gga cga gga gag agg gtc atc tcc ttc cat gtg atc agg ggt    1929
Lys Ala Gly Arg Gly Glu Arg Val Ile Ser Phe His Val Ile Arg Gly
535                 540                 545 cct gaa att act gtg caa cct gct gcc cag cca act gag cag gag agt    1977
Pro Glu Ile Thr Val Gln Pro Ala Ala Gln Pro Thr Glu Gln Glu Ser
550                 555                 560 gtg tcc ctg ttg tgc act gca gac aga aat acg ttt gag aac ctc acg    2025
Val Ser Leu Leu Cys Thr Ala Asp Arg Asn Thr Phe Glu Asn Leu Thr
565                 570                 575                 580 tgg tac aag ctt ggc tca cag gca aca tcg gtc cac atg ggc gaa tca    2073
Trp Tyr Lys Leu Gly Ser Gln Ala Thr Ser Val His Met Gly Glu Ser
                585                 590                 595 ctc aca cca gtt tgc aag aac ttg gat gct ctt tgg aaa ctg aat ggc    2121
Leu Thr Pro Val Cys Lys Asn Leu Asp Ala Leu Trp Lys Leu Asn Gly
        600                 605                 610 acc atg ttt tct aac agc aca aat gac atc ttg att gtg gca ttt cag    2169
Thr Met Phe Ser Asn Ser Thr Asn Asp Ile Leu Ile Val Ala Phe Gln
615                 620                 625 aat gcc tct ctg cag gac caa ggc gac tat gtt tgc tct gct caa gat    2217
Asn Ala Ser Leu Gln Asp Gln Gly Asp Tyr Val Cys Ser Ala Gln Asp
630                 635                 640 aag aag acc aag aaa aga cat tgc ctg gtc aaa cag ctc atc atc cta    2265
Lys Lys Thr Lys Lys Arg His Cys Leu Val Lys Gln Leu Ile Ile Leu
645                 650                 655                 660 gag cgc atg gca ccc atg atc acc gga aat ctg gag aat cag aca aca    2313
Glu Arg Met Ala Pro Met Ile Thr Gly Asn Leu Glu Asn Gln Thr Thr
                665                 670                 675 acc att ggc gag acc att gaa gtg act tgc cca gca tct gga aat cct    2361
Thr Ile Gly Glu Thr Ile Glu Val Thr Cys Pro Ala Ser Gly Asn Pro
        680                 685                 690 acc cca cac att aca tgg ttc aaa gac aac gag acc ctg gta gaa gat    2409
Thr Pro His Ile Thr Trp Phe Lys Asp Asn Glu Thr Leu Val Glu Asp
695                 700                 705 tca ggc att gta ctg aga gat ggg aac cgg aac ctg act atc cgc agg    2457
Ser Gly Ile Val Leu Arg Asp Gly Asn Arg Asn Leu Thr Ile Arg Arg
710                 715                 720 gtg agg aag gag gat gga ggc ctc tac acc tgc cag gcc tgc aat gtc    2505
Val Arg Lys Glu Asp Gly Gly Leu Tyr Thr Cys Gln Ala Cys Asn Val
725                 730                 735                 740 ctt ggc tgt gca aga gcg gag acg ctc ttc ata ata gaa ggt gcc cag    2553
Leu Gly Cys Ala Arg Ala Glu Thr Leu Phe Ile Ile Glu Gly Ala Gln
                745                 750                 755 gaa aag acc aac ttg gaa gtc att atc ctc gtc ggc act gca gtg att    2601
Glu Lys Thr Asn Leu Glu Val Ile Ile Leu Val Gly Thr Ala Val Ile
        760                 765                 770 gcc atg ttc ttc tgg ctc ctt ctt gtc att gtc cta cgg acc gtt aag    2649
Ala Met Phe Phe Trp Leu Leu Leu Val Ile Val Leu Arg Thr Val Lys
775                 780                 785
```

-continued

| | |
|---|---|
| cgg gcc aat gaa ggg gaa ctg aag aca ggc tac ttg tct att gtc atg<br>Arg Ala Asn Glu Gly Glu Leu Lys Thr Gly Tyr Leu Ser Ile Val Met<br>790                     795                    800 | 2697 |
| gat cca gat gaa ttg ccc ttg gat gag cgc tgt gaa cgc ttg cct tat<br>Asp Pro Asp Glu Leu Pro Leu Asp Glu Arg Cys Glu Arg Leu Pro Tyr<br>805                     810                    815                    820 | 2745 |
| gat gcc agc aag tgg gaa ttc ccc agg gac cgg ctg aaa cta gga aaa<br>Asp Ala Ser Lys Trp Glu Phe Pro Arg Asp Arg Leu Lys Leu Gly Lys<br>                    825                    830                    835 | 2793 |
| cct ctt ggc cgc ggt gcc ttc ggc caa gtg att gag gca gac gct ttt<br>Pro Leu Gly Arg Gly Ala Phe Gly Gln Val Ile Glu Ala Asp Ala Phe<br>840                     845                    850 | 2841 |
| gga att gac aag aca gcg act tgc aaa aca gta gcc gtc aag atg ttg<br>Gly Ile Asp Lys Thr Ala Thr Cys Lys Thr Val Ala Val Lys Met Leu<br>855                     860                    865 | 2889 |
| aaa gaa gga gca aca cac agc gag cat cga gcc ctc atg tct gaa ctc<br>Lys Glu Gly Ala Thr His Ser Glu His Arg Ala Leu Met Ser Glu Leu<br>870                     875                    880 | 2937 |
| aag atc ctc atc cac att ggt cac cat ctc aat gtg gtg aac ctc cta<br>Lys Ile Leu Ile His Ile Gly His His Leu Asn Val Val Asn Leu Leu<br>885                     890                    895                    900 | 2985 |
| ggc gcc tgc acc aag ccg gga ggg cct ctc atg gtg att gtg gaa ttc<br>Gly Ala Cys Thr Lys Pro Gly Gly Pro Leu Met Val Ile Val Glu Phe<br>                    905                    910                    915 | 3033 |
| tgc aag ttt gga aac cta tca act tac tta cgg ggc aag aga aat gaa<br>Cys Lys Phe Gly Asn Leu Ser Thr Tyr Leu Arg Gly Lys Arg Asn Glu<br>920                     925                    930 | 3081 |
| ttt gtt ccc tat aag agc aaa ggg gca cgc ttc cgc cag ggc aag gac<br>Phe Val Pro Tyr Lys Ser Lys Gly Ala Arg Phe Arg Gln Gly Lys Asp<br>                    935                    940                    945 | 3129 |
| tac gtt ggg gag ctc tcc gtg gat ctg aaa aga cgc ttg gac agc atc<br>Tyr Val Gly Glu Leu Ser Val Asp Leu Lys Arg Arg Leu Asp Ser Ile<br>950                     955                    960 | 3177 |
| acc agc agc cag agc tct gcc agc tca ggc ttt gtt gag gag aaa tcg<br>Thr Ser Ser Gln Ser Ser Ala Ser Ser Gly Phe Val Glu Glu Lys Ser<br>965                     970                    975                    980 | 3225 |
| ctc agt gat gta gag gaa gaa gaa gct tct gaa gaa ctg tac aag gac<br>Leu Ser Asp Val Glu Glu Glu Glu Ala Ser Glu Glu Leu Tyr Lys Asp<br>                    985                    990                    995 | 3273 |
| ttc ctg acc ttg gag cat ctc atc tgt tac agc ttc caa gtg gct aag<br>Phe Leu Thr Leu Glu His Leu Ile Cys Tyr Ser Phe Gln Val Ala Lys<br>1000                  1005                1010 | 3321 |
| ggc atg gag ttc ttg gca tca agg aag tgt atc cac agg gac ctg gca<br>Gly Met Glu Phe Leu Ala Ser Arg Lys Cys Ile His Arg Asp Leu Ala<br>1015                  1020                1025 | 3369 |
| gca cga aac att ctc cta tcg gag aag aat gtg gtt aag atc tgt gac<br>Ala Arg Asn Ile Leu Leu Ser Glu Lys Asn Val Val Lys Ile Cys Asp<br>1030                  1035                1040 | 3417 |
| ttc ggc ttg gcc cgg gac att tat aaa gac ccg gat tat gtc aga aaa<br>Phe Gly Leu Ala Arg Asp Ile Tyr Lys Asp Pro Asp Tyr Val Arg Lys<br>1045                  1050                1055                1060 | 3465 |
| gga gat gcc cga ctc cct ttg aag tgg atg gcc ccg gaa acc att ttt<br>Gly Asp Ala Arg Leu Pro Leu Lys Trp Met Ala Pro Glu Thr Ile Phe<br>                    1065                1070                1075 | 3513 |
| gac aga gta tac aca att cag agc gat gtg tgg tct ttc ggt gtg ttg<br>Asp Arg Val Tyr Thr Ile Gln Ser Asp Val Trp Ser Phe Gly Val Leu<br>1080                  1085                1090 | 3561 |
| ctc tgg gaa ata ttt tcc tta ggt gcc tcc cca tac cct ggg gtc aag<br>Leu Trp Glu Ile Phe Ser Leu Gly Ala Ser Pro Tyr Pro Gly Val Lys | 3609 |

```
                    1095                1100                    1105
att gat gaa gaa ttt tgt agg aga ttg aaa gaa gga act aga atg cgg      3657
Ile Asp Glu Glu Phe Cys Arg Arg Leu Lys Glu Gly Thr Arg Met Arg
         1110                1115                    1120 gct cct gac tac act acc cca gaa atg tac cag acc atg ctg gac tgc      3705
Ala Pro Asp Tyr Thr Thr Pro Glu Met Tyr Gln Thr Met Leu Asp Cys
1125                1130                    1135                1140 tgg cat gag gac ccc aac cag aga ccc tcg ttt tca gag ttg gtg gag      3753
Trp His Glu Asp Pro Asn Gln Arg Pro Ser Phe Ser Glu Leu Val Glu
             1145                1150                    1155 cat ttg gga aac ctc ctg caa gca aat gcg cag cag gat ggc aaa gac      3801
His Leu Gly Asn Leu Leu Gln Ala Asn Ala Gln Gln Asp Gly Lys Asp
                1160                1165                    1170 tat att gtt ctt cca atg tca gag aca ctg agc atg gaa gag gat tct      3849
Tyr Ile Val Leu Pro Met Ser Glu Thr Leu Ser Met Glu Glu Asp Ser
             1175                1180                    1185 gga ctc tcc ctg cct acc tca cct gtt tcc tgt atg gag gaa gag gaa      3897
Gly Leu Ser Leu Pro Thr Ser Pro Val Ser Cys Met Glu Glu Glu Glu
         1190                1195                    1200 gtg tgc gac ccc aaa ttc cat tat gac aac aca gca gga atc agt cat      3945
Val Cys Asp Pro Lys Phe His Tyr Asp Asn Thr Ala Gly Ile Ser His
1205                1210                    1215                1220 tat ctc cag aac agt aag cga aag agc cgg cca gtg agt gta aaa aca      3993
Tyr Leu Gln Asn Ser Lys Arg Lys Ser Arg Pro Val Ser Val Lys Thr
             1225                1230                    1235 ttt gaa gat atc cca ttg gag gaa cca gaa gta aaa gtg atc cca gat      4041
Phe Glu Asp Ile Pro Leu Glu Glu Pro Glu Val Lys Val Ile Pro Asp
                1240                1245                    1250 gac agc cag aca gac agt ggg atg gtc ctt gca tca gaa gag ctg aaa      4089
Asp Ser Gln Thr Asp Ser Gly Met Val Leu Ala Ser Glu Glu Leu Lys
             1255                1260                    1265 act ctg gaa gac agg aac aaa tta tct cca tct ttt ggt gga atg atg      4137
Thr Leu Glu Asp Arg Asn Lys Leu Ser Pro Ser Phe Gly Gly Met Met
         1270                1275                    1280 ccc agt aaa agc agg gag tct gtg gcc tcg gaa ggc tcc aac cag acc      4185
Pro Ser Lys Ser Arg Glu Ser Val Ala Ser Glu Gly Ser Asn Gln Thr
1285                1290                    1295                1300 agt ggc tac cag tct ggg tat cac tca gat gac aca gac acc acc gtg      4233
Ser Gly Tyr Gln Ser Gly Tyr His Ser Asp Asp Thr Asp Thr Thr Val
             1305                1310                    1315 tac tcc agc gac gag gca gga ctt tta aag atg gtg gat gct gca gtt      4281
Tyr Ser Ser Asp Glu Ala Gly Leu Leu Lys Met Val Asp Ala Ala Val
                1320                1325                    1330 cac gct gac tca ggg acc aca ctg cag ctc acc tcc tgt tta aat gga      4329
His Ala Asp Ser Gly Thr Thr Leu Gln Leu Thr Ser Cys Leu Asn Gly
             1335                1340                    1345 agt ggt cct gtc ccg gct ccg ccc cca act cct gga aat cac gag aga      4377
Ser Gly Pro Val Pro Ala Pro Pro Pro Thr Pro Gly Asn His Glu Arg
         1350                1355                    1360 ggt gct gct tag attttcaagt gttgttcttt ccaccacccg gaagtagcca         4429
Gly Ala Ala
1365 catttgattt tcattttttgg aggagggacc tcagactgca aggagcttgt cctcagggca   4489 tttccagaga agatgcccat gacccaagaa tgtgttgact ctactctctt ttccattcat   4549 ttaaaagtcc tatataatgt gccctgctgt ggtctcacta ccagttaaag caaaagactt   4609 tcaaacacgt ggactctgtc ctccaagaag tggcaacggc acctctgtga aactggatcg   4669 aatgggcaat gctttgtgtg ttgaggatgg gtgagatgtc ccagggccga gtctgtctac   4729
```

```
cttggaggct tgtgtggagga tgcgggctat gagccaagtg ttaagtgtgg gatgtggact    4789
gggaggaagg aaggcgcaag tcgctcggag agcggttgga gcctgcagat gcattgtgct    4849
ggctctggtg gaggtgggct tgtggcctgt caggaaacgc aaaggcggcc ggcagggttt    4909
ggttttggaa ggtttgcgtg ctcttcacag tcgggttaca ggcgagttcc ctgtggcgtt    4969
tcctactcct aatgagagtt ccttccggac tcttacgtgt ctcctggcct ggccccagga    5029
aggaaatgat gcagcttgct ccttcctcat ctctcaggct gtgccttaat tcagaacacc    5089
aaaagagagg aacgtcggca gaggctcctg acggggccga agaattgtga aacagaaca    5149 gaaactcagg gtttctgctg ggtggagacc cacgtggcgc cctggtggca ggtctgaggg    5209
ttctctgtca agtggcggta aaggctcagg ctggtgttct tcctctatct ccactcctgt    5269
caggccccca agtcctcagt attttagctt tgtggcttcc tgatggcaga aaaatcttaa    5329
ttggttggtt tgctctccag ataatcacta gccagatttc gaaattactt tttagccgag    5389
gttatgataa catctactgt atcctttaga attttaacct ataaaactat gtctactggt    5449
ttctgcctgt gtgcttatgt t                                              5470
```

<210> SEQ ID NO 11
<211> LENGTH: 25
<212> TYPE: DNA
<213> ORGANISM: Artificial Sequence
<220> FEATURE:
<223> OTHER INFORMATION: PCR Primer

<400> SEQUENCE: 11
gagttcacac aaagcctttt attgc                                           25

<210> SEQ ID NO 12
<211> LENGTH: 26
<212> TYPE: DNA
<213> ORGANISM: Artificial Sequence
<220> FEATURE:
<223> OTHER INFORMATION: PCR Primer

<400> SEQUENCE: 12
taactgagat acttcacagg gattcg                                          26

<210> SEQ ID NO 13
<211> LENGTH: 24
<212> TYPE: DNA
<213> ORGANISM: Artificial Sequence
<220> FEATURE:
<223> OTHER INFORMATION: PCR Probe

<400> SEQUENCE: 13
cttgactgcc cactgtggct tcca                                            24

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                                 20

<210> SEQ ID NO 15
<211> LENGTH: 20
<212> TYPE: DNA

<210> SEQ ID NO 16
<211> LENGTH: 27
<212> TYPE: DNA
<213> ORGANISM: Artificial Sequence
<220> FEATURE:
<223> OTHER INFORMATION: PCR Primer

<400> SEQUENCE: 15
gggtctcgct cctggaagat                                          20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                  27

<210> SEQ ID NO 17
<211> LENGTH: 1267
<212> TYPE: DNA
<213> ORGANISM: Homo sapiens
<220> FEATURE:
<221> NAME/KEY: CDS
<222> LOCATION: (1084)...(1150)

<400> SEQUENCE: 17
cctccttccc ctgggcctaa ggatatcttg gctggaagct ctgctctgaa aaggggcatg    60
gccaaacttt cactagggct cttcgttggg gagcacgatg acaaaagcc ttcttggggc   120 taggcaggtc acttcaaact tggagccgcc aaatattttg ggaaatagcg ggaatgctgg   180
cgaactgggc aagtgcgttt tctgattaag agcaaccaga ttcagctttt taaactacaa   240
ttatactggc caaacaaaat acccttatac aaaaaccaaa actactggca ggagtcgctg   300
ccagcttgcg acccggcata cttggctgag tatccgcttc tcccttgtgg ctccaaactg   360
ctgcagattc tcggccactt cagacgcgcg cgatggcgaa gagggtcctg cactttgacg   420
cgcctggtga gggagcggtg ctcttcgcag cgctcctggt gatgctcccc aaatttcggg   480
gaccggcaag cgattaaatc ttggagttgc tcagcgcccg ttaccgagta ctttttattt   540
acaccagaaa caaagttgtt gctctgggat gttctctcct gggcgacttg gggcccagcg   600
cagtccagtt gtgtgggaa atgggagat gtaaatgggc ttggggagct ggagatcccc     660
gccgggtacc cggtgaggg gcggggctgg ccgcacggga gagccctcc tccgccccgg     720 ccccgccccg catggccccg cctccgcgct ctagagtttc ggctccagct cccaccctgc   780
actgagtccc gggaccccgg gagagcggtc agtgtgtggt cgctgcgttt cctctgcctg    840
cgccgggcat cacttgcgcg ccgcagaaag tccgtctggc agcctggata tcctctccta    900
ccggcacccg cagacgcccc tgcagccgcc ggtcggcgcc cgggctccct agccctgtgc    960
gctcaactgt cctgcgctgc ggggtgccgc gagttccacc tccgcgcctc cttctctaga   1020
caggcgctgg gagaaagaac cggctcccga gttctgggca tttcgcccgg ctcgaggtgc   1080 agg atg cag agc aag gtg ctg ctg gcc gtc gcc ctg tgg ctc tgc gtg    1128
    Met Gln Ser Lys Val Leu Leu Ala Val Ala Leu Trp Leu Cys Val
    1               5                  10                  15 gag acc cgg gcc gcc tct gtg ggtaaggagc ccactctgga ggaggaaggc        1179
Glu Thr Arg Ala Ala Ser Val
                20 agacaggtcg ggtgagggcg gagaggacct gaaagccaga tctaactcgg aatcgtagag   1239 ctggagagtt ggacaggact tgacatt                                       1267

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tgatgcccgg cgcaggcaga                                                   20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
taggagagga tatccaggct                                                   20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gttgagcgca cagggctagg                                                   20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ttggccagta taattgtagt                                                   20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
agccgggcga aatgcccaga                                                   20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ttgctctgca tcctgcacct                                                   20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 24
actaggcaaa cccacagagg                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ccaggcgcgt caaagtgcag                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ctctgtcccc tgcaagtaat                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
attgggccaa agccagtcca                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
caactccaag atttaatcgc                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
aagcacttgt aggctccagt                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gcacaaagtg acacgttgag                                              20

<210> SEQ ID NO 31
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
ggaacaaatc tcttttctgg                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gctgtcccag gaaattctgt                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tttaagacaa gcttttctcc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ctgtacaatt taagacaagc                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ttcttgctgt acaatttaag                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ctccagagtg ggctccttac                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
```
ggctttcagg tcctctccgc                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tagatctggc tttcaggtcc                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gcctggcagg tgtagaggcc                    20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
tgggcacctt ctattatgaa                    20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ttttcctggg caccttctat                    20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ccagaagaac atggcaatca                    20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
attggcccgc ttaacggtcc                    20

<210> SEQ ID NO 44
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 44
tagcctgtct tcagttcccc                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gacaagtagc ctgtcttcag                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
agttcatctg gatccatgac                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ttggccaaag gcaccacggc                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tcaatcactt ggccaaaggc                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gctgtcttgt caattccaaa                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gtgttgctcc ttctttcaac                                               20
```

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ctggtgatgc tgtccaagcg                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tccaaggtca ggaagtcctt                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
gatgctccaa ggtcaggaag                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gatgagatgc tccaaggtca                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
taacagatga gatgctccaa                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
agctgtaaca gatgagatgc                                               20

<210> SEQ ID NO 57
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 57
cttggaagct gtaacagatg                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cttagccact tggaagctgt                    20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tgccaagaac tccatgccct                    20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ttttaaccac gttcttctcc                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
cacagatttt aaccacgttc                    20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
agcacctaag gaaaatattt                    20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
atggtctggt acatttctgg                    20

```
<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ttgccatcct gctgagcatt                                          20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
agaatcctct tccatgctca                                          20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
agtccagaat cctcttccat                                          20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gaaacaggtg aggtaggcag                                          20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
tacaggaaac aggtgaggta                                          20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ctccatacag gaaacaggtg                                          20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 70
ttgtcataat ggaatttggg                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gctgtgttgt cataatggaa                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ttcctgctgt gttgtcataa                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
actgattcct gctgtgttgt                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ggctctttcg cttactgttc                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ttcaaatgtt tttacactca                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gggatatctt caaatgtttt                                              20

<210> SEQ ID NO 77
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 77
ttttcagctc ttctgaggca                                                    20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ccaaaagatg gagataattt                                                    20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
cattccacca aaagatggag                                                    20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gccacagact ccctgctttt                                                    20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
acggtggtgt ctgtgtcatc                                                    20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
agtacacggt ggtgtctgtg                                                    20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
```

-continued gcttccttttt aaacaggagg                                                20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
acctctcatg tgatgtccgg                                                 20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
ttcaaaatct gagcagacct                                                 20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tggtggaaag aacaacactt                                                 20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
aatcaaatgc ggctacttcc                                                 20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
aatgaaaatc aaatgcggct                                                 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
caggatatgc ctagaagact                                                 20

<210> SEQ ID NO 90
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 90
ttccacactt aaggcttggc                                                 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
acaatgcatt tgcaggctcc                                                 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
aaccccgtct gaacccttta                                                 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
aaggaactct cattaggagt                                                 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
agccagagct gcatcatttt                                                 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
acagactata aatatatgtg                                                 20
```

ANTISENSE MODULATION OF VASCULAR ENDOTHELIAL GROWTH FACTOR RECEPTOR-2 EXPRESSION

FIELD OF THE INVENTION

The present invention provides compositions and methods for modulating the expression of vascular endothelial growth factor receptor-2. In particular, this invention relates to compounds, particularly oligonucleotides, specifically hybridizable with nucleic acids encoding vascular endothelial growth factor receptor-2. Such compounds have been shown to modulate the expression of vascular endothelial growth factor receptor-2.

BACKGROUND OF THE INVENTION

As a mitogen that acts primarily on endothelial cells, vascular endothelial growth factor (VEGF, or VEGF-A) is essential for endothelial cell differentiation (vasculogenesis) and for the sprouting of new capillaries from pre-existing vessels (angiogenesis) during embryonic development and wound repair. Signaling by VEGF affects a number of biological functions, including endothelial cell survival via inhibition of apoptosis, cell proliferation, vascular permeability, monocyte activation, chemotaxis, and cell migration. Thus, VEGF is believed to play a key role in wound healing, postnatal angiogenesis during pregnancy, and in human pathophysiological conditions such as cancer, rheumatoid arthritis, ocular neovascular disorders, and cardiovascular disease (Zachary and Gliki, *Cardiovasc. Res.,* 2001, 49, 568–581).

For transmission of the VEGF signal, VEGF binds to three receptor protein tyrosine kinases, vascular endothelial growth factor receptors-1, -2, and -3, that are structurally related to the PDGF family of class III receptors, characterized by cytoplasmic regions with an insert sequence within the catalytic domain, a single transmembrane domain, and seven immunoglobulin-like extracellular domains. Monomeric vascular endothelial growth factor receptors have 100-fold less affinity for VEGF, and thus, ligands preferentially bind to predimerized receptors. Upon ligand binding, the receptors auto- or trans-phosphorylate specific cytoplasmic tyrosine residues to initiate an intracellular cascade of signaling that ultimately reaches nuclear transcription factor effectors (Zachary and Gliki, *Cardiovasc. Res.,* 2001, 49, 568–581).

Most biological functions of VEGF are mediated through vascular endothelial growth factor receptor-2, and the role of vascular endothelial growth factor receptor-1 is currently less well understood (Zachary and Gliki, *Cardiovasc. Res.,* 2001, 49, 568–581).

Human vascular endothelial growth factor receptor-2 (also known as VEGF receptor-2, VEGFR2, kinase insert domain receptor, KDR, tyrosine kinase growth factor receptor, and FLK1) binds VEGF, albeit with weaker affinity than does vascular endothelial growth factor receptor-1, and specifically binds VEGF-E, VEGF-C and VEGF-D (alternative splice forms of VEGF), but does not bind the closely related placenta growth factor (PlGF) (Shibuya, *Int. J. Biochem. Cell Biol.,* 2001, 33, 409–420; Zachary and Gliki, *Cardiovasc. Res.,* 2001, 49, 568–581).

The vascular endothelial growth factor receptor-2 gene was cloned using a PCR approach in which degenerate primers were designed based on the conserved kinase domains flanking the insert domain (characteristic of type III receptor tyrosine kinases). A PCR product was then amplified from a human endothelial cell cDNA library and the product was used as a probe to isolate two overlapping clones (together comprising the entire gene) from that cDNA library (Terman et al., *Oncogene,* 1991, 6, 1677–1683). The vascular endothelial growth factor receptor-2 gene was mapped to the 4q12 human chromosomal locus in a cluster of protein tyrosine kinases including two other type III receptor genes, KIT (mast/stem cell growth factor receptor) and PDGFRA (platelet derived growth factor receptor, A-type) (Spritz et al., *Genomics,* 1994, 22, 431–436).

Disclosed and claimed in U.S. Pat. No. 6,204,011 is an isolated nucleic acid molecule encoding human vascular endothelial growth factor receptor-2 and purified forms of the encoded protein, as well as recombinant expression vectors, a process for the expression of the vascular endothelial growth factor receptor-2 protein, and host cells which express the protein (Kendall et al., 2001).

A degenerate PCR approach was also used to amplify sequences from the kinase domains of the mouse vascular endothelial growth factor receptor-2 gene, using cDNAs synthesized from total RNA from mouse cell populations enriched for hematopoietic stem and progenitor cells. These PCR products were then used to clone the cDNA encoding vascular endothelial growth factor receptor-2 from a library constructed from day 12.5 whole mouse embryo, and the gene was mapped to mouse chromosome 5 (Matthews et al., *Proc. Natl. Acad. Sci. U.S.A.,* 1991, 88, 9026–9030).

Vascular endothelial growth factor receptor-1 may act as a negative regulator of vascular endothelial growth factor receptor-2. Differential splicing of the vascular endothelial growth factor receptor-1 transcript results in a full-length receptor and a naturally occurring, soluble form of the extracellular domain of vascular endothelial growth factor receptor-1 (sVEGFR-1 or sFLT-1). This sFLT-1 isoform can form heterodimers with vascular endothelial growth factor receptor-2 (Kendall et al., *Biochem. Biophys. Res. Commun.,* 1996, 226, 324–328), and when overexpressed, sFLT-1 but not an artificial, soluble vascular endothelial growth factor receptor-2, can act as a receptor antagonist and inhibit VEGF-induced cell proliferation and migration of human microvascular endothelial cells and human umbilical vein endothelial cells (HUVECs) by forming and inactive complex with VEGF and with full length vascular endothelial growth factor receptor-2 (Roeckl et al., *Exp. Cell Res.,* 1998, 241, 161–170; Zachary and Gliki, *Cardiovasc. Res.,* 2001, 49, 568–581).

Like other receptor protein kinases, vascular endothelial growth factor receptor-2 associates with a number of src homology 2 (SH2) domain-containing proteins, including the adapter proteins Grb2, Nck, and Shc, as well as the protein tyrosine phosphatases, SHP-1 and SHP-2, involved in a multitude of signal transduction pathways (Zachary and Gliki, *Cardiovasc. Res.,* 2001, 49, 568–581). It has also been suggested that vascular endothelial growth factor receptor-2 may be unique among receptor tyrosine kinases in potentially activating the MAPK/ERK kinase cascade via a Ras-independent mechanism mediated by protein kinase C (Wu et al., *J. Biol. Chem.,* 2000, 275, 5096–5103).

Expression of VEGF receptor-2 was once believed to be restricted to proliferating endothelial cells (Millauer et al., *Nature,* 1994, 367, 576–579; Millauer et al., *Cell,* 1993, 72, 835–846; Shalaby et al., *Nature,* 1995, 376, 62–66), but expression of both VEGF receptor-1 and VEGF receptor-2 has been demonstrated more recently in atherosclerotic lesions and in several non-endothelial tumor cell types (Epstein et al., *Cardiovasc. Res.,* 2001, 49, 532–542). For example, co-expression of both receptors with VEGF is found in melanoma cells derived from primary and metastatic lesions (Graeven et al., *J. Cancer Res. Clin. Oncol.*, 1999, 125, 621–629). Vascular endothelial growth factor receptor-2 is also believed to be important in development and maintenance of glomerular capillaries (Robert et al., *Am. J. Physiol. Renal Physiol.*, 2000, 279, F275–282).

The majority of severe visual loss in the United States results from complications associated with retinal neovascularization, in patients with ischemic ocular diseases such as diabetic retinopathy, retinal vein occlusion and retinopathy of prematurity. VEGF and its receptors have been shown to have a causal role in retinal angiogenesis (Aiello et al., *Proc. Natl. Acad. Sci. U.S.A.*, 1995, 92, 10457–10461). Furthermore, in experimentally induced choroidal neovascularization (CNV), a devastating complication of macular diseases such as age-related macular degeneration, expression levels of both VEGF and vascular endothelial growth factor receptor-2 were shown to increase, and thus, vascular endothelial growth factor receptor-2 may play a role in the pathologic process of CNV (Wada et al., *Curr. Eye Res.*, 1999, 18, 203–213).

VEGF is thought to be the single most important cytokine in cancer and other types of pathological angiogenesis, and the neurotransmitter dopamine has been shown, at nontoxic levels, to strongly and selectively inhibit the vascular permeabilizing and angiogenic activities of VEGF. Recently, dopamine was shown to act as a potent inhibitor of VEGF signaling by inducing endocytosis of vascular endothelial growth factor receptor-2 (Basu et al., *Nat. Med.*, 2001, 7, 569–574). There is also evidence that tissues immediately surrounding growing tumors and other active sites of angiogenesis, such as in rheumatoid arthritis, have reduced sympathetic innervation, and that dopamine concentration in malignant tumors is significantly reduced. Thus, vascular endothelial growth factor receptor-2 mediated angiogenesis may be linked to neurotransmitter activity (Basu et al., *Nat. Med.*, 2001, 7, 569–574).

In human postnatal hematopoetic stem cells, up to 0.5% of CD34+ cells express vascular endothelial growth factor receptor-2, whereas lineage committed hematopoetic progenitor cells did not express vascular endothelial growth factor receptor-2, indicating that this receptor serves as a positive functional marker for defining stem cells and distinguishing them from progenitors (Ziegler et al., *Science*, 1999, 285, 1553–1558).

Kaposi sarcoma (KS) is the most common tumor associated with HIV-1 infection, developing in nearly 30% of all cases. Characteristics of these KS tumors are abnormal vascularization and the proliferation of endothelial cells and spindle (tumor) cells. Vascular endothelial growth factor receptor-2 is expressed at high levels in AIDS-KS cell lines, while normal skin cells from the same patients did not express vascular endothelial growth factor receptor-2, suggesting that vascular endothelial growth factor receptor-2 plays a role in the development and progression of KS (Masood et al., *Proc. Natl. Acad. Sci. U.S.A.*, 1997, 94, 979–984).

A dominant negative mutant of mouse vascular endothelial growth factor receptor-2 was constructed in a recombinant retroviral vector and used to infect C6 rat glioblastoma target cells in vivo, to show that tumor growth could be prevented by overexpression of this dominant negative mutant of vascular endothelial growth factor receptor-2 (Millauer et al., *Nature*, 1994, 367, 576–579).

Mice deficient in vascular endothelial growth factor receptor-2 have been generated by disruption of the gene using homologous recombination in embryonic stem cells, and these mice produce neither differentiated endothelial cells nor organized blood vessels. Embryos homozygous for this mutation die in utero as a result of a defect in the development of hematopoietic and endothelial cells; thus, vascular endothelial growth factor receptor-2 is essential for hematopoesis and vascular development in mice (Shalaby et al., *Nature*, 1995, 376, 62–66). Nevertheless, vascular endothelial growth factor receptor-2 null stem cells are able to differentiate into hematopoietic and endothelial cells in vitro, but they give rise to a greatly reduced number of blast colonies and subsequent migration and clonal expansion require vascular endothelial growth factor receptor-2 (Schuh et al., *Proc. Natl. Acad. Sci. U.S.A.*, 1999, 96, 2159–2164).

The modulation of vascular endothelial growth factor receptor-2 activity and/or expression is an ideal target for therapeutic intervention aimed at regulating the VEGF signaling pathway in the prevention and treatment of cancer, cardiovascular disease, ocular neovascular disorders such as diabetic retinopathy, and rheumatoid arthritis.

Disclosed and claimed in PCT Publication WO 94/11499 are a recombinant DNA vector containing a nucleotide sequence that encodes vascular endothelial growth factor receptor-2 operationally associated with a regulatory sequence that controls gene expression in a host, as well as an oligonucleotide which encodes an antisense sequence complementary to a portion of the vascular endothelial growth factor receptor-2 nucleotide sequence. Further claimed is a monoclonal antibody with immunospecifically binds to an epitope of vascular endothelial growth factor receptor-2 and competitively inhibits the binding of VEGF, as well as methods for screening and identifying antagonists of VEGF (Ullrich et al., 1994).

Disclosed and claimed in U.S. Pat. No. 6,177,401 are a method for inhibiting angiogenesis and/or vasculogenesis in a subject in need thereof, comprising administering a therapeutically effective amount of an organic compound that inhibits VEGF-binding, tyrosine phosphorylation, or enzymatic activity of the human or murine vascular endothelial growth factor receptor-2 protein. Further claimed are methods for treating a disease associated with vascular endothelial growth factor receptor-2 mediated proliferation of blood vessels in a mammal, wherein the disease is a solid tumor, rheumatoid arthritis, retinopathy (Ullrich et al., 2001).

Disclosed and claimed in U.S. Pat. No. 5,851,999 is a pharmaceutical composition comprising a vector expressing a polynucleotide having a functional human or murine vascular endothelial growth factor receptor-2 extracellular and transmembrane domain, and a deleted or mutated cytoplasmic domain so that the encoded polypeptide is signaling-incompetent and renders endogenous wild type vascular endothelial growth factor receptor-2 unresponsive to VEGF. Further claimed is a method of treating a disease state which is associated with vascular endothelial growth factor receptor-2 mediated proliferation of blood vessels in a mammal, comprising administering said pharmaceutical composition to the mammal, wherein the disease state is rheumatoid arthritis, retinopathy, and solid tumors, as well as a method for inhibiting VEGF-induced proliferation of an endothelial cell, comprising administering pharmaceutical compositions or an organic compound that inhibits the enzymatic activity of vascular endothelial growth factor receptor-2 (Ullrich et al., 1998).

Disclosed and claimed in PCT Publication WO 01/44460 is an isolated recombinant polynucleotide, wherein greater than or equal to 55 nucleotides of the sequence have greater than 80% identity to the transcriptional control and enhancer elements of mouse vascular endothelial growth factor receptor-2 gene locus. Further claimed are an expression cassette comprising said polynucleotide and a reporter sequence, and a vector containing the polynucleotide and the reporter sequence, as well as a method for monitoring the expression of angiogenesis-related genes in a living transgenic rodent and methods for identifying compounds that affect angiogenesis, wherein the effect is an increase or a decrease in expression of said angiogenesis-related gene and the compound is a candidate for inhibiting or stimulating angiogenesis (Contag et al., 2001).

Disclosed and claimed in U.S. Pat. No. 5,861,484 are naturally occurring or recombinantly engineered soluble VEGF receptor-related inhibitor proteins comprising truncated and modified forms of vascular endothelial growth factor receptor-2 as well as a composition comprising said inhibitors and a pharmaceutically acceptable carrier (Kendall and Thomas, 1999).

Disclosed and claimed in PCT Publication WO 00/75319 are nucleic acid constructs encoding chimeric fusions of VEGF receptor-1 and VEGF receptor-2 polypeptide sequences, having improved pharmacokinetic properties, as well as methods of making and using said chimeric polypeptides to decrease or inhibit plasma leakage and/or vascular permeability in a mammal (Papadopoulos. Nicholas et al., 2000).

Disclosed and claimed in U.S. Pat. No. 5,830,880 is a recombinant DNA construct for the prophylaxis or therapy of tumor diseases, which comprises an activator sequence, a cell cycle regulated promoter module, and a DNA sequence encoding an anti-tumor substance, wherein the activator sequence is a promoter for vascular endothelial growth factor receptor-2 (Sedlacek et al., 1998).

Disclosed and claimed in U.S. Pat. No. 5,747,651 are isolated, monoclonal antibodies that bind specifically to the extracellular portion of human or murine vascular endothelial growth factor receptor-2 (Lemischka, 1998).

Use of a blocking antibody to functionally inactivate vascular endothelial growth factor receptor-2 disrupts ongoing angiogenesis and prevents invasiveness of malignant cells without reducing tumor cell proliferation. This reversion of a malignant to a benign phenotype by halting angiogenesis demonstrates a key role for vascular endothelial growth factor receptor-2 in carcinoma cell invasiveness (Skobe et al., Nat. Med., 1997, 3, 1222–1227).

Two phosphorothioate antisense oligonucleotides, both 18 nucleotides in length, complementary to bovine vascular endothelial growth factor receptor-2, were used to inhibit gene expression and show that the mitogenic, chemotactic, and platelet activating factor-stimulating activities of VEGF on bovine aortic endothelial cells were dependent on vascular endothelial growth factor receptor-2 but not on vascular endothelial growth factor receptor-1 (Bernatchez et al., J. Biol. Chem., 1999, 274, 31047–31054).

A phosphorothioate antisense oligonucleotide, 15 nucleotides in length, targeted on the translation initiation codon of vascular endothelial growth factor receptor-2 was used inhibit its expression and demonstrate that a lack of vascular endothelial growth factor receptor-2 abolishes the mitogenic response to VEGF in neonatal hemangioma cells (Berard et al., Am. J. Pathol., 1997, 150, 1315–1326).

In addition to its mitogenic effects, VEGF has been observed in increased levels in the brain after an ischemic event, and is predicted to have a neuroprotective effect against glutamate toxicity. When an antisense oligonucleotide targeting vascular endothelial growth factor receptor-2 was used to inhibit its expression in hippocampal neurons, it was concluded that there are two independent anti-apoptotic pathways in adult brain mediated by VEGF receptors-1 and -2, and that the neuroprotective effect is mediated by vascular endothelial growth factor receptor-2 (Matsuzaki et al., Faseb J., 2001, 12, 12).

An antisense S-oligonucleotide, 18 nucleotides in length, specific to vascular endothelial growth factor recpetor-2 was used as a positive control to block capillary-like tubular network formation in human endothelial cells (Henderson et al., J. Biol. Chem., 2001, 276, 6169–6176).

Investigative strategies aimed at studying vascular endothelial growth factor receptor-2 function have involved the use of specific function-blocking antibodies, antisense oligonucleotides, chimeric fusion proteins, and transgenic animals and vectors expressing polypeptide variants or truncated forms of vascular endothelial growth factor receptor-2.

Currently, there are no known therapeutic agents that effectively inhibit the synthesis of vascular endothelial growth factor receptor-2. Consequently, there remains a long felt need for agents capable of effectively inhibiting vascular endothelial growth factor receptor-2 function.

Antisense technology is emerging as an effective means for reducing the expression of specific gene products and therefore may prove to be uniquely useful in a number of therapeutic, diagnostic, and research applications for the modulation of vascular endothelial growth factor receptor-2 expression.

The present invention provides compositions and methods for modulating vascular endothelial growth factor receptor-2 expression.

SUMMARY OF THE INVENTION

The present invention is directed to compounds, particularly antisense oligonucleotides, which are targeted to a nucleic acid encoding vascular endothelial growth factor receptor-2, and which modulate the expression of vascular endothelial growth factor receptor-2. Pharmaceutical and other compositions comprising the compounds of the invention are also provided. Further provided are methods of modulating the expression of vascular endothelial growth factor receptor-2 in cells or tissues comprising contacting said cells or tissues with one or more of the antisense compounds or compositions of the invention. Further provided are methods of treating an animal, particularly a human, suspected of having or being prone to a disease or condition associated with expression of vascular endothelial growth factor receptor-2 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding vascular endothelial growth factor receptor-2, ultimately modulating the amount of vascular endothelial growth factor receptor-2 produced. This is accomplished by providing antisense compounds which specifically hybridize with one or more nucleic acids encoding vascular endothelial growth factor receptor-2. As used herein, the terms "target nucleic acid" and "nucleic acid encoding vascular endothelial growth factor receptor-2" encompass DNA encoding vascular endothelial growth factor receptor-2, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of vascular endothelial growth factor receptor-2. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding vascular endothelial growth factor receptor-2. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding vascular endothelial growth factor receptor-2, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'–5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nONH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$-CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'- dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of vascular endothelial growth factor receptor-2 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding vascular endothelial growth factor receptor-2, enabling sandwich and other assays to easily be constructed to exploit this fact. Hybridization of the antisense oligonucleotides of the invention with a nucleic acid encoding vascular endothelial growth factor receptor-2 can be detected by means known in the art. Such means may include conjugation of an enzyme to the oligonucleotide, radiolabelling of the oligonucleotide or any other suitable detection means. Kits using such detection means for detecting the level of vascular endothelial growth factor receptor-2 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, l-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and triglycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1\text{-}10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers.

However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis
Deoxy and 2'-Alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., Helvetica Chimica Acta, 1995, 78, 486–504.

2,2'-Anhydro[1-(Beta-D-Arabinofuranosyl)-5-Methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-Methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-Dimethoxytrityl-5-Methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-Methoxyethyl-5'-O-Dimethoxytrityl-5-Methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-Methoxyethyl-5'-O-Dimethoxytrityl-5-Methyl-4-Triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-Dimethoxytrityl-5-Methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-Methoxyethyl-5'-O-Dimethoxytrityl-5-Methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-Methoxyethyl-5'-O-Dimethoxytrityl-5-Methylcytidine-3'-Amidite

N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(Dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-Anhydro-5-Methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-Hydroxyethyl)-5-Methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-Phthalimidoxy)Ethyl]-5'-t-Butyldiphenylsilyl-5-Methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-Tert-Butyldiphenylsilyl-2'-O-[(2-Formadoximinooxy) Ethyl]-5-Methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirrred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-Dimethylaminooxyethyl]-5-Methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(Dimethylaminooxyethyl)-5-Methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(Dimethylaminooxyethyl)-5-Methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-Dimethylaminooxyethyl)-5-Methyluridine-3'-[(2-Cyanoethyl)-N,N-Diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-Isobutyryl-6-O-Diphenylcarbamoyl-2'-O-(2-Ethylacetyl)-5'-O-(4,4'-Dimethoxytrityl)Guanosine-3'-[(2-Cyanoethyl)-N,N-Diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-Dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—N($CH_2$)$_2$, or 2'-DMAEOE nucleoside amidites) are prepared as follows. Other nucleoside amidites are prepared similarly.

2'-O-[2(2-N,N-Dimethylaminoethoxy)Ethyl]-5-Methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-Dimethoxytrityl-2'-O-[2(2-N,N-Dimethylaminoethoxy) Ethyl)]-5-Methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-Dimethylaminoethoxy)-Ethyl)]-5-Methyl Uridine-3'-O-(Cyanoethyl-N,N-Diisopropyl)Phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-Deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-Deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-Deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HuVEC Cells:

The human umbilical vein endothilial cell line HuVEC was obtained from the American Type Culure Collection (Manassas, Va.). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 µL OPTI-MEM™-L reduced-serum medium (Gibco BRL) and then treated with 130 µL of OPTI-MEM™-1 containing 3.75 µg/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Vascular Endothelial Growth Factor Receptor-2 Expression Antisense modulation of vascular endothelial growth factor receptor-2 expression can be assayed in a variety of ways known in the art. For example, vascular endothelial growth factor receptor-2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of vascular endothelial growth factor receptor-2 can be quantitated in a variety of ways well known in the art, such as immunoprecipitation, Western blot analysis (immunoblotting), ELISA or fluorescence-activated cell sorting (FACS). Antibodies directed to vascular endothelial growth factor receptor-2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11
Poly(A)+ mRNA Isolation

Poly(A)+ mRNA was isolated according to Miura et al., *Clin. Chem.,* 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12
Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-Time Quantitative PCR Analysis of Vascular Endothelial Growth Factor Receptor-2 mRNA Levels Quantitation of vascular endothelial growth factor receptor-2 mRNA levels was determined by real-time quantitative PCR using the ABI PRIS™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM MgCl$_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human vascular endothelial growth factor receptor-2 were designed to hybridize to a human vascular endothelial growth factor receptor-2 sequence, using published sequence information (GenBank accession number AF035121, incorporated herein as SEQ ID NO:3). For human vascular endothelial growth factor receptor-2 the PCR primers were:

```
forward primer:
AACCAGACAAGCGGCTACCA          (SEQ ID NO:4)

reverse primer:
CTCCAATCTCTATCAGCTTTAAAAGTTCT (SEQ ID NO:5)
``` and the PCR probe was: FAM-CACTCCGATGACACAGACACCACCG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

```
forward primer:
GAAGGTGAAGGTCGGAGTC           (SEQ ID NO:7)

reverse primer:
GAAGATGGTGATGGGATTTC          (SEQ ID NO:8)
``` and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse vascular endothelial growth factor receptor-2 were designed to hybridize to a mouse vascular endothelial growth factor receptor-2 sequence, using published sequence information (GenBank accession number X70842, incorporated herein as SEQ ID NO:10). For mouse vascular endothelial growth factor receptor-2 the PCR primers were:

```
forward primer:
GGCAAATTCAACGGCACAGT          (SEQ ID NO:11)

reverse primer:
TAACTGAGATACTTCACAGGGATTCG    (SEQ ID NO:12)
``` and the PCR probe was: FAM-CTTGACTGCCCACTGTGGCTTCCA-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were:

```
forward primer:
GGCAAATTCAACGGCACAGT          (SEQ ID NO:14)

reverse primer:
GGGTCTCGCTCCTGGAAGAT          (SEQ ID NO:15)
``` and the PCR probe was: 5' JOE-AAGGCCGAGAATGGGAAGCTTGTCATC-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of Vascular Endothelial Growth Factor Receptor-2 mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human vascular endothelial growth factor receptor-2, a human vascular endothelial growth factor receptor-2 specific probe was prepared by PCR using the

```
forward primer
AACCAGACAAGCGGCTACCA          (SEQ ID NO:4)

and the reverse primer
CTCCAATCTCTATCAGCTTTAAAAGTTCT. (SEQ ID NO:5)
```

To normalize for variations in loading and transfer efficiency membranes were stripped and probed for human glyceraldehyde-3-phosphate dehydrogenase (GAPDH) RNA (Clontech, Palo Alto, Calif.).

To detect mouse vascular endothelial growth factor receptor-2, a mouse vascular endothelial growth factor receptor-2 specific probe was prepared by PCR using the forward primer GAGTTCACACAAAGCCTTTTATTGC (SEQ ID NO: 11) and the reverse primer TAACTGAGATACTTCACAGGGATTCG (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human Vascular Endothelial Growth Factor Receptor-2 Expression by Chimeric Phosphorothioate Oligonucleotides Having 2'-MOE Wings and a Deoxy Gap In accordance with the present invention, a series of oligonucleotides were designed to target different regions of the human vascular endothelial growth factor receptor-2 RNA, using published sequences (GenBank accession number AF035121, incorporated herein as SEQ ID NO: 3, and GenBank accession number X89776, incorporated herein as SEQ ID NO: 17). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human vascular endothelial growth factor receptor-2 mRNA levels by quantitative real-time PCR as described in other examples herein. Data are averages from two experiments. If present, "N.D." indicates "no data".

TABLE 1

Inhibition of human vascular endothelial growth factor receptor-2 mRNA levels by chimeric phosphorothioate oligonucleotides having 2'-MOE wings and a deoxy gap

| ISIS # | REGION | TARGET SEQ ID NO | TARGET SITE | SEQUENCE | %_INHIB | SEQ ID NO |
|---|---|---|---|---|---|---|
| 142100 | 5' UTR | 3 | 53 | tgatgcccggcgcaggcaga | 69 | 18 |
| 142101 | 5' UTR | 3 | 101 | taggagaggatatccaggct | 60 | 19 |
| 142102 | 5' UTR | 3 | 168 | gttgagcgcacagggctagg | 25 | 20 |
| 142103 | 5' UTR | 17 | 234 | ttggccagtataattgtagt | 4 | 21 |
| 142104 | 5' UTR | 3 | 273 | agccgggcgaaatgcccaga | 64 | 22 |
| 142105 | Start Codon | 3 | 295 | ttgctctgcatcctgcacct | 81 | 23 |
| 142106 | Coding | 3 | 362 | actaggcaaacccacagagg | 48 | 24 |
| 142107 | 5' UTR | 17 | 408 | ccaggcgcgtcaaagtgcag | 24 | 25 |
| 142108 | Coding | 3 | 454 | ctctgtccctgcaagtaat | 59 | 26 |
| 142109 | Coding | 3 | 479 | attgggccaaagccagtcca | 94 | 27 |
| 142110 | 5' UTR | 17 | 490 | caactccaagatttaatcgc | 11 | 28 |
| 142111 | Coding | 3 | 595 | aagcacttgtaggctccagt | 85 | 29 |
| 142112 | Coding | 3 | 772 | gcacaaagtgacacgttgag | 77 | 30 |
| 142113 | Coding | 3 | 799 | ggaacaaatctcttttctgg | 41 | 31 |
| 142114 | Coding | 3 | 827 | gctgtcccaggaaattctgt | 47 | 32 |
| 142115 | Coding | 3 | 1018 | tttaagacaagcttttctcc | 80 | 33 |
| 142116 | Coding | 3 | 1026 | ctgtacaatttaagacaagc | 80 | 34 |
| 142117 | Coding | 3 | 1032 | ttcttgctgtacaatttaag | 71 | 35 |
| 142118 | 5' UTR | 17 | 1151 | ctccagagtgggctccttac | 66 | 36 |
| 142119 | 5' UTR | 17 | 1197 | ggctttcaggtcctctccgc | 64 | 37 |
| 142120 | 5' UTR | 17 | 1204 | tagatctggctttcaggtcc | 57 | 38 |
| 142121 | Coding | 3 | 2500 | gcctggcaggtgtagaggcc | 56 | 39 |
| 142122 | Coding | 3 | 2557 | tgggcaccttctattatgaa | 52 | 40 |
| 142123 | Coding | 3 | 2563 | ttttcctgggcaccttctat | 53 | 41 |
| 142124 | Coding | 3 | 2621 | ccagaagaacatggcaatca | 86 | 42 |
| 142125 | Coding | 3 | 2663 | attggcccgcttaacggtcc | 64 | 43 |
| 142126 | Coding | 3 | 2686 | tagcctgtcttcagttcccc | 84 | 44 |
| 142127 | Coding | 3 | 2692 | gacaagtagcctgtcttcag | 58 | 45 |
| 142128 | Coding | 3 | 2716 | agttcatctggatccatgac | 66 | 46 |
| 142129 | Coding | 3 | 2825 | ttggccaaaggcaccacggc | 78 | 47 |
| 142130 | Coding | 3 | 2833 | tcaatcacttggccaaaggc | 76 | 48 |
| 142131 | Coding | 3 | 2863 | gctgtcttgtcaattccaaa | 62 | 49 |
| 142132 | Coding | 3 | 2910 | gtgttgctccttctttcaac | 63 | 50 |
| 142133 | Coding | 3 | 3187 | ctggtgatgctgtccaagcg | 67 | 51 |
| 142134 | Coding | 3 | 3292 | tccaaggtcaggaagtcctt | 76 | 52 |
| 142135 | Coding | 3 | 3297 | gatgctccaaggtcaggaag | 62 | 53 |
| 142136 | Coding | 3 | 3302 | gatgagatgctccaaggtca | 78 | 54 |
| 142137 | Coding | 3 | 3307 | taacagatgagatgctccaa | 74 | 55 |
| 142138 | Coding | 3 | 3312 | agctgtaacagatgagatgc | 70 | 56 |
| 142139 | Coding | 3 | 3318 | cttggaagctgtaacagatg | 57 | 57 |
| 142140 | Coding | 3 | 3326 | cttagccacttggaagctgt | 81 | 58 |
| 142141 | Coding | 3 | 3344 | tgccaagaactccatgccct | 76 | 59 |
| 142142 | Coding | 3 | 3414 | ttttaaccacgttcttctcc | 69 | 60 |
| 142143 | Coding | 3 | 3420 | cacagattttaaccacgttc | 87 | 61 |
| 142144 | Coding | 3 | 3593 | agcacctaaggaaaatattt | 29 | 62 |
| 142145 | Coding | 3 | 3700 | atggtctggtacatttctgg | 69 | 63 |
| 142146 | Coding | 3 | 3802 | ttgccatcctgctgagcatt | 63 | 64 |
| 142147 | Coding | 3 | 3854 | agaatcctcttccatgctca | 80 | 65 |
| 142148 | Coding | 3 | 3859 | agtccagaatcctcttccat | 54 | 66 |
| 142149 | Coding | 3 | 3883 | gaaacaggtgaggtaggcag | 64 | 67 |
| 142150 | Coding | 3 | 3888 | tacaggaaacaggtgaggta | 56 | 68 |
| 142151 | Coding | 3 | 3893 | ctccatacaggaaacaggtg | 61 | 69 |
| 142152 | Coding | 3 | 3931 | ttgtcataatggaatttggg | 22 | 70 |
| 142153 | Coding | 3 | 3937 | gctgtgttgtcataatggaa | 59 | 71 |
| 142154 | Coding | 3 | 3942 | ttcctgctgtgttgtcataa | 64 | 72 |
| 142155 | Coding | 3 | 3947 | actgattcctgctgtgttgt | 37 | 73 |

TABLE 1-continued

Inhibition of human vascular endothelial growth factor receptor-2 mRNA
levels by chimeric phosphorothioate oligonucleotides
having 2'-MOE wings and a deoxy gap

| ISIS # | REGION | TARGET SEQ ID NO | TARGET SITE | SEQUENCE | %_INHIB | SEQ ID NO |
|---|---|---|---|---|---|---|
| 142156 | Coding | 3 | 3978 | ggctctttcgcttactgttc | 86 | 74 |
| 142157 | Coding | 3 | 4004 | ttcaaatgttttacactca | 56 | 75 |
| 142158 | Coding | 3 | 4012 | gggatatcttcaaatgtttt | 23 | 76 |
| 142159 | Coding | 3 | 4095 | ttttcagctcttctgaggca | 67 | 77 |
| 142160 | Coding | 3 | 4132 | ccaaaagatggagataattt | 30 | 78 |
| 142161 | Coding | 3 | 4139 | cattccaccaaaagatggag | 39 | 79 |
| 142162 | Coding | 3 | 4168 | gccacagactccctgctttt | 66 | 80 |
| 142163 | Coding | 3 | 4237 | acggtggtgtctgtgtcatc | 84 | 81 |
| 142164 | Coding | 3 | 4242 | agtacacggtggtgtctgtg | 69 | 82 |
| 142165 | Stop Codon | 3 | 4363 | gcttccttttaaacaggagg | 50 | 83 |
| 142166 | 5' UTR | 3 | 4399 | acctctcatgtgatgtccgg | 66 | 84 |
| 142167 | 5' UTR | 3 | 4415 | ttcaaaatctgagcagacct | 11 | 85 |
| 142168 | 5' UTR | 3 | 4433 | tggtggaaagaacaacactt | 70 | 86 |
| 142169 | 5' UTR | 3 | 4456 | aatcaaatgcggctacttcc | 70 | 87 |
| 142170 | 5' UTR | 3 | 4462 | aatgaaaatcaaatgcggct | 63 | 88 |
| 142171 | 5' UTR | 3 | 4519 | caggatatgcctagaagact | 46 | 89 |
| 142172 | 5' UTR | 3 | 4836 | ttccacacttaaggcttggc | 88 | 90 |
| 142173 | 5' UTR | 3 | 4906 | acaatgcatttgcaggctcc | 84 | 91 |
| 142174 | 5' UTR | 3 | 4968 | aaccccgtctgaacccttta | 80 | 92 |
| 142175 | 5' UTR | 3 | 5053 | aaggaactctcattaggagt | 34 | 93 |
| 142176 | 5' UTR | 3 | 5111 | agccagagctgcatcatttt | 49 | 94 |
| 142177 | 5' UTR | 3 | 5662 | acagactataaatatatgtg | 43 | 95 |

As shown in Table 1, SEQ ID NOs 18, 19, 20, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94 and 95 demonstrated at least 20% inhibition of human vascular endothelial growth factor receptor-2 expression in this assay and are therefore preferred. The target sites to which these preferred sequences are complementary are herein referred to as "active sites" and are therefore preferred sites for targeting by compounds of the present invention.

Example 16
Antisense Inhibition of Mouse Vascular Endothelial growth Factor Receptor-2 Expression by Chimeric Phosphorothioate Oligonucleotides Having 2'-MOE Wings and a Deoxy Gap.

In accordance with the present invention, a second series of oligonucleotides were designed to target different regions of the mouse vascular endothelial growth factor receptor-2 RNA, using published sequences (GenBank accession number X70842, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse vascular endothelial growth factor receptor-2 mRNA levels by quantitative real-time PCR as described in other examples herein. Data are averages from two experiments. If present, "N.D." indicates "no data".

TABLE 2

Inhibition of mouse vascular endothelial growth factor
receptor-2 mRNA levels by chimeric phosphorothioate
oligonucleotides having 2'-MOE wings and a deoxy gap

| ISIS # | REGION | TARGET SEQ ID NO | TARGET SITE | SEQUENCE | %_INHIB | SEQ ID NO |
|---|---|---|---|---|---|---|
| 142109 | Coding | 10 | 461 | attgggccaaagccagtcca | 73 | 27 |
| 142113 | Coding | 10 | 787 | ggaacaaatctctttctgg | 51 | 31 |
| 142114 | Coding | 10 | 815 | gctgtcccaggaaattctgt | 54 | 32 |
| 142121 | Coding | 10 | 2476 | gcctggcaggtgtagaggcc | 24 | 39 |
| 142122 | Coding | 10 | 2533 | tgggcaccttctattatgaa | 15 | 40 |
| 142123 | Coding | 10 | 2539 | ttttcctgggcaccttctat | 6 | 41 |
| 142124 | Coding | 10 | 2597 | ccagaagaacatggcaatca | 36 | 42 |
| 142125 | Coding | 10 | 2639 | attggcccgcttaacggtcc | 53 | 43 |
| 142126 | Coding | 10 | 2662 | tagcctgtcttcagttcccc | 66 | 44 |
| 142127 | Coding | 10 | 2668 | gacaagtagcctgtcttcag | 48 | 45 |

TABLE 2-continued

Inhibition of mouse vascular endothelial growth factor
receptor-2 mRNA levels by chimeric phosphorothioate
oligonucleotides having 2'-MOE wings and a deoxy gap

| ISIS # | REGION | TARGET SEQ ID NO | TARGET SITE | SEQUENCE | %_INHIB | SEQ ID NO |
|---|---|---|---|---|---|---|
| 142131 | Coding | 10 | 2839 | gctgtcttgtcaattccaaa | 67 | 49 |
| 142132 | Coding | 10 | 2886 | gtgttgctccttctttcaac | 59 | 50 |
| 142133 | Coding | 10 | 3163 | ctggtgatgctgtccaagcg | 48 | 51 |
| 142134 | Coding | 10 | 3268 | tccaaggtcaggaagtcctt | 45 | 52 |
| 142135 | Coding | 10 | 3273 | gatgctccaaggtcaggaag | 44 | 53 |
| 142136 | Coding | 10 | 3278 | gatgagatgctccaaggtca | 51 | 54 |
| 142137 | Coding | 10 | 3283 | taacagatgagatgctccaa | 41 | 55 |
| 142138 | Coding | 10 | 3288 | agctgtaacagatgagatgc | 41 | 56 |
| 142139 | Coding | 10 | 3294 | cttggaagctgtaacagatg | 21 | 57 |
| 142140 | Coding | 10 | 3302 | cttagccacttggaagctgt | 51 | 58 |
| 142141 | Coding | 10 | 3320 | tgccaagaactccatgccct | 63 | 59 |
| 142145 | Coding | 10 | 3676 | atggtctggtacatttctgg | 31 | 63 |
| 142147 | Coding | 10 | 3830 | agaatcctcttccatgctca | 60 | 65 |
| 142148 | Coding | 10 | 3835 | agtccagaatcctcttccat | 34 | 66 |
| 142149 | Coding | 10 | 3859 | gaaacaggtgaggtaggcag | 23 | 67 |
| 142150 | Coding | 10 | 3864 | tacaggaaacaggtgaggta | 38 | 68 |
| 142151 | Coding | 10 | 3869 | ctccatacaggaaacaggtg | 46 | 69 |
| 142152 | Coding | 10 | 3907 | ttgtcataatggaatttggg | 15 | 70 |
| 142153 | Coding | 10 | 3913 | gctgtgttgtcataatggaa | 26 | 71 |
| 142154 | Coding | 10 | 3918 | ttcctgctgtgttgtcataa | 35 | 72 |
| 142155 | Coding | 10 | 3923 | actgattcctgctgtgttgt | 37 | 73 |
| 142156 | Coding | 10 | 3954 | ggctctttcgcttactgttc | 69 | 74 |
| 142157 | Coding | 10 | 3980 | ttcaaatgtttttacactca | 16 | 75 |
| 142158 | Coding | 10 | 3988 | gggatatcttcaaatgtttt | 34 | 76 |
| 142160 | Coding | 10 | 4108 | ccaaaagatggagataattt | 14 | 78 |
| 142161 | Coding | 10 | 4115 | cattccaccaaaagatggag | 20 | 79 |
| 142162 | Coding | 10 | 4144 | gccacagactccctgctttt | 65 | 80 |
| 142163 | Coding | 10 | 4213 | acggtggtgtctgtgtcatc | 51 | 81 |
| 142164 | Coding | 10 | 4218 | agtacacggtggtgtctgtg | 36 | 82 |
| 142168 | 3' UTR | 10 | 4396 | tggtggaaagaacaacactt | 42 | 86 |
| 142175 | 3' UTR | 10 | 4974 | aaggaactctcattaggagt | 36 | 93 |

As shown in Table 2, SEQ ID NOs 27, 31, 32, 42, 43, 44, 56, 49, 50, 51, 52, 53, 54, 55, 56, 58, 59, 63, 65, 66, 68, 69, 72, 73, 74, 76, 80, 81, 82, 86 and 93 demonstrated at least 30% inhibition of mouse vascular endothelial growth factor receptor-2 expression in this experiment and are therefore preferred. The target sites to which these preferred sequences are complementary are herein referred to as "active sites" and are therefore preferred sites for targeting by compounds of the present invention.

Example 17
Western Blot Analysis of Vascular Endothelial Growth Factor Receptor-2 Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to vascular endothelial growth factor receptor-2 is used, with a radio-labelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to nucleobases 53 through 187 or nucleobases 273 through 292 of a 5'-untranslated region, nucleobases 362 through 381, nucleobases 454 through 473, nucleobases 479 through 498, nucleobases 595 through 614, nucleobases 772 through 791, nucleobases 799 through 818, nucleobases 827 through 846, nucleobases 2500 through 2519, nucleobases 2557 through 2582, nucleobases 2621 through 2640, nucleobases 2663 through 2682, nucleobases 2686 through 2711, nucleobases 2716 through 2735, nucleobases 2825 through 2852, nucleobases 2663 through 2882, nucleobases 2910 through 2929, nucleobases 3187 through 3206, nucleobases 3292 through 3363, nucleobases 3414 through 3439, nucleobases 3593 through 3612, nucleobases 3700 through 3719, nucleobases 3802 through 3821, nucleobases 3254 through 3878, nucleobases 3883 through 3912, nucleobases 3931 through 3966, nucleobases 3978 through 3997, nucleobases 4004 through 4031, nucleobases 4095 through 4114, nucleobases 4132 through 4158, or nucleobases 4168 through 4187 of a coding region, nucleobases 4363 through 4382 of a stop codon region, or nucleobases 4399 through 5681 of a 3'-untranslated region of a nucleic acid molecule encoding vascular endothelial growth factor receptor-2 of SEQ ID NO: 3, wherein said compound comprises at least one modified internucleoside linkage, specifically hybridizes with one of said regions and inhibits the expression of vascular endothelial growth factor receptor-2.

2. The compound of claim 1 which is an antisense oligonucleotide.

3. The compound of claim 1 wherein the modified internucleoside linkage is a phosphorothioate linkage.

4. The compound of claim 2 wherein the antisense oligonucleotide comprises at least one modified sugar moiety.

5. The compound of claim 4 wherein the modified sugar moiety is a 2'-o-methoxyethyl sugar moiety.

6. The compound of claim 2 wherein the antisense oligonucleotide comprises at least one modified nucleobase.

7. The compound of claim 6 wherein the modified nucleobase is a 5-methylcytosine.

8. The compound of claim 2 wherein the antisense oligonucleotide is a chimeric oligonucleotide.

9. A composition comprising the compound of claim 1 and a pharmaceutically acceptable carrier or diluent.

10. The composition of claim 9 further comprising a colloidal dispersion system.

11. The composition of claim 9 wherein the compound is an antisense oligonucleotide.

12. A method of inhibiting the expression of vascular endothelial growth factor receptor-2 in cells or tissues comprising contacting said cells or tissues in vitro with the compound of claim 1 so that expression of vascular endothelial growth factor receptor-2 is inhibited.

* * * * *